(12) United States Patent
Lin

(10) Patent No.: US 7,322,821 B1
(45) Date of Patent: Jan. 29, 2008

(54) POSITIONING DEVICE FOR DENTAL IMPLANT

(76) Inventor: Hsieh-Hsing Lin, 2F, No. 86, Sanmin Rd., Sindian City, Taipei Hsien (TW)

( * ) Notice: Subject to any disclaimer, the term of this patent is extended or adjusted under 35 U.S.C. 154(b) by 0 days.

(21) Appl. No.: 11/520,243

(22) Filed: Sep. 13, 2006

(51) Int. Cl.
*A61C 9/00* (2006.01)
*A61C 3/00* (2006.01)
*A61C 5/00* (2006.01)
*A61C 5/04* (2006.01)
*A61C 8/00* (2006.01)
*A61B 5/117* (2006.01)

(52) U.S. Cl. ............ 433/72; 433/75; 433/215; 433/225; 433/229; 433/201.1

(58) Field of Classification Search ............ 433/72, 433/75, 215, 225, 229, 201.1
See application file for complete search history.

(56) References Cited

U.S. PATENT DOCUMENTS

| | | | |
|---|---|---|---|
| 5,718,579 A | * | 2/1998 | Kennedy ............ 433/75 |
| 5,743,916 A | | 4/1998 | Greenberg et al. |
| 5,833,693 A | | 11/1998 | Abrahami |
| 5,888,065 A | | 3/1999 | Sussman |
| 5,989,025 A | | 11/1999 | Conley |
| 7,097,451 B2 | | 8/2006 | Tang |

\* cited by examiner

*Primary Examiner*—Samchuan C. Yao
*Assistant Examiner*—Yogesh P Patel
(74) *Attorney, Agent, or Firm*—Alan Kamrath; Kamrath & Associates PA

(57) ABSTRACT

A positioning device for dental implant has a post and multiple guides. The post is cylindrical and has a diameter corresponding to a diameter of a hole in a dental model. The guides are mounted detachably on the post and are semi-tubular tabs and each has an inner concave, an inner diameter, and an outer diameter. The guides are mounted concentrically one another. A dentist can use the positioning device to precisely position a drill bit of a drilling device on an edentulous place of a patient's jaw bone and drills a bone cavity suitable for a dental implant. The drill bit can be easily inserted into the patient's mouth without opening excessively.

6 Claims, 31 Drawing Sheets

POSITIONING DEVICE FOR DENTAL IMPLANT

BACKGROUND OF THE INVENTION

1. Field of the Invention

The present invention relates to a positioning device for a dental implant, and especially to a positioning device for conveniently making a resin guide bridge and accurately positioning a dental implant in a dental model and a jaw bone in a patient's mouth.

2. Description of the Related Art

Making an artificial tooth in place of a person's damaged tooth is a conventional treatment. However, the conventional treatment has following disadvantages:

1. When a single damaged tooth is extracted and replaced with an artificial tooth, grinding the adjacent natural teeth is necessary so the ground teeth may be used as two supports to hold the artificial tooth. However, the adjacent natural teeth are injured when ground. To avoid the injury to the adjacent natural teeth, a denture may be fixed by metal clasps hooking the adjacent teeth. However, the exposed metal clasps may disfigure the appearance of the teeth.

2. When multiple damaged teeth are replaced with a denture having multiple artificial teeth, few remaining natural teeth support the denture. These remaining natural teeth are pressed strongly when a user chews food and grits the teeth and therefore injure the gums and periodontal tissue.

To avoid the disadvantages of the conventional dental treatment, dental implantation is used to substitute for the treatment. With reference FIGS. 22 and 31, a method of dental implantation is drilling a bone cavity (623A) in an edentulous place of the jaw bone (6A) out of which a damaged tooth removed in a patient's mouth by drilling the edentulous place of the jaw bone (6A). Next, a dental implant (64A) made of titanium is inserted into the bone cavity (623A) and the wound of the bone cavity (623A) in the jaw bone is sutured. After the fixture is integrated, an abutment (65A) screwed on the dental implant (64A) and then a crown (66A) put on the abutment (65A). Since the dental implant (64A) and the abutment (65A) support the crown (66A), the crown (66A) can sustain the force of occlusion.

The depth for which the dental implant (64A) is inserted into the jaw bone and the position in which the dental implant (64A) is located is critical to succeed in the fixed dental implantation. The correct arrangement of the dental implant (64A) is not only the position but also the angulation of the bone cavity (623A) opposite to the upper tooth or the lower tooth so a top (661A) of the crown (66A) fits the corresponding tooth. If the position or the angulation of the bone cavity (623A) is inaccurate, the crown (66A) will not fit the corresponding tooth.

The bone cavity must precisely correspond to the dental implant. When the bone cavity is too small, the dental implant cannot be inserted into the bone cavity. When the bone cavity is overlarge, the dental implant cannot be positioned securely in the bone cavity. Therefore, a multiple sets of drills and resin guide bridges are used to enlarge the bone cavity step by step.

With reference to FIGS. 23 to 25 and 29, a dentist drills a first hole (62) in an edentulous place of a dental model (6) and inserts a first post (7) into the first hole (62). Wax or gypsum is filled in the gap of the teeth to block out the undercut. Then resin is coated on the edentulous place (61) and covers teeth adjacent to the edentulous place (61) to form a first resin guide bridge (8) with a first through hole (81). After the resin hardens, the dentist replaces the first post (7) with a first guide tube (9). The first guide tube (9) is longer than the through hole (81). A diameter of the first guide tube (9) corresponds to a diameter of a first drill bit (101) of a drilling device (10).

With reference to FIGS. 26 to 28, the dentist drills a hole (62) again to enlarge the first hole (62) in sequent to form a fourth hole (623) and manufactures a fourth resin guide bridge (8C) to obtain the multiple sets of the resin guide bridge (8, 8C) and guide tube (9, 93).

With reference to FIGS. 29 and 30, the dentist puts the first resin guide bridge (8) with the first guide tube (9) on an edentulous place (61A) and adjacent teeth on a patient's jaw bone (6A). Because an inner surface of the first resin guide bridge (9) corresponds to the edentulous place (61A) and the adjacent teeth, the first guide tube (9) is precisely located in a point which will be drilled to form a bone cavity (62) later. The dentist then drills the first bone cavity (62A) by the drilling device (10) with the first drill bit (101). Then the dentist takes away the first resin guide bridge (9) and puts a second resin guide bridge to enlarge the bone cavity with a second drill bit. A fourth resin guide bridge (8C) is put on the edentulous place (61A) and the teeth on the patient's jaw bone (6A) to drill a fourth bone cavity (623A) by a fourth drill bit (104) through a fourth guide tube (93), so the dental implant can be inserted into the bone cavity.

However, the above method for implanting the dental implant has following disadvantages:

1. A drill bit of a drilling device must move over the bridge to follow the guide tube so that the patient needs to open mouth wider. A patient with a small mouth or having a damaged tooth in the posterior area suffers greatly from excessively opening his mouth to place the drilling device into the mouth.

2. The dentist needs to stop drilling the bone cavity to measure the depth of the bone cavity.

3. Manufacture of the resin guide bridge is complex because the dentist needs to repeatedly drill the hole and insert the different size of the posts into the holes to manufacture the resin guide bridge.

4. Lacks of outer irrigation may cause the temperature elevated, thus impacted the osteointegration of the implant.

SUMMARY OF THE INVENTION

The objective of the present invention is to provide a positioning device for dental implant that can be conveniently to form a resin guide bridge and accurately positioning dental implant in a dental model and a jaw bone in a patient's mouth.

To achieve the foregoing objective, a positioning device for a dental implant in accordance with the present invention has a post and multiple guides. The post is cylindrical and has a diameter corresponding to a diameter of a hole in a dental model. The guides are mounted detachably on the post and are semi-tubular tabs and each guide has an inner concave, an inner diameter, and an outer diameter. The guides are mounted concentrically one another.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
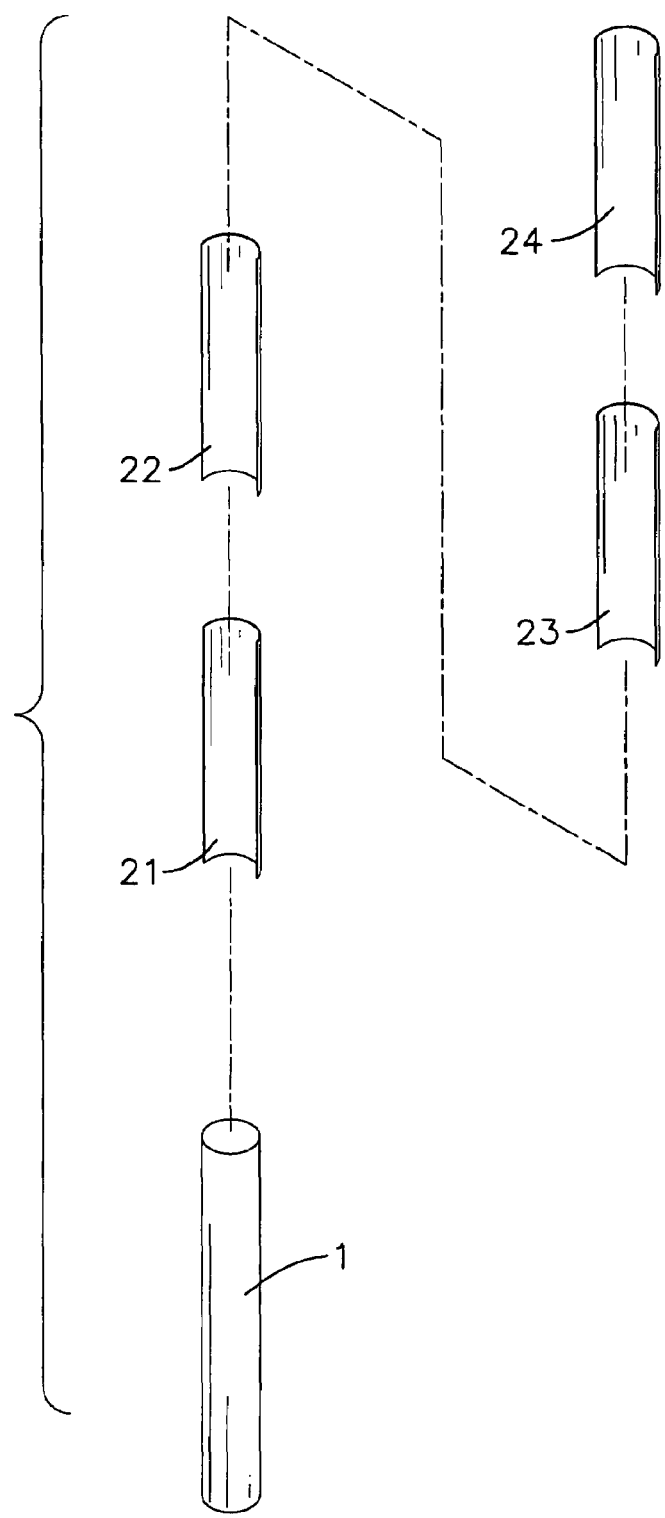
FIG. 1 is a perspective view of a positioning device for a dental implant in accordance with the present invention.
Figure 2:
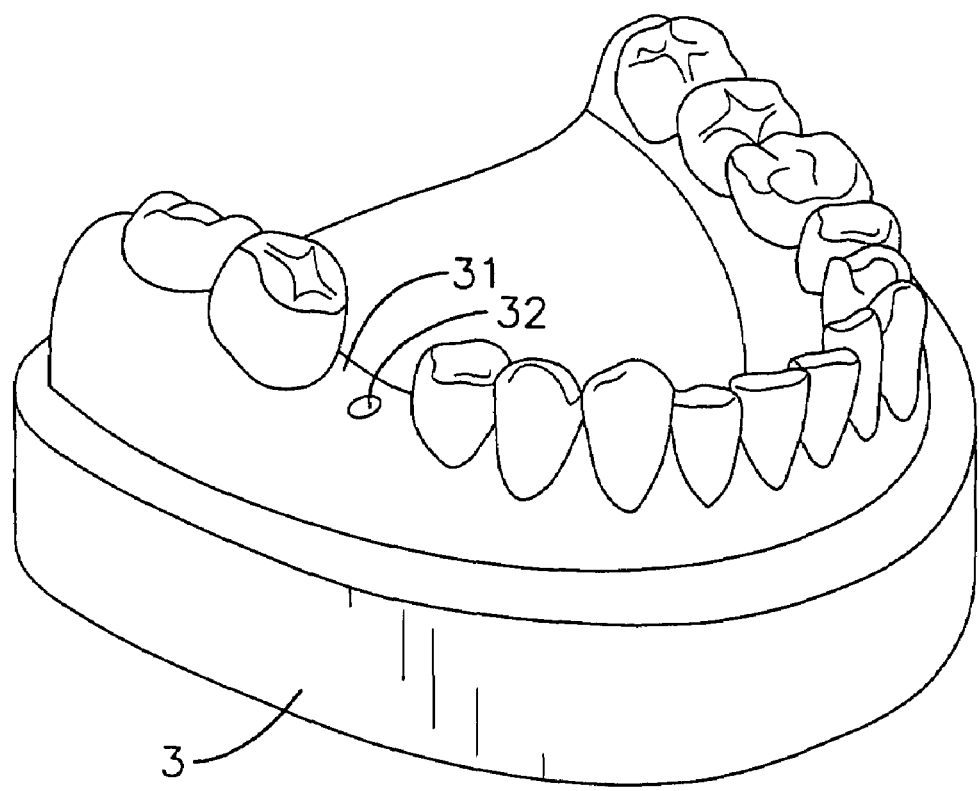
FIG. 2 is a perspective view of a dental model with a hole corresponding to the positioning device in FIG. 1.

With reference to FIGS. 1 and 2, a positioning device for a dental implant in accordance with the present invention is used with a dental model (3) having a hole (32) defined in dental model (3). The positioning device comprises a post (1) and multiple guides (21, 22, 23, 24).

The post (1) is cylindrical, comprises a diameter and may be made of magnetic material or permeable material. The diameter of the post (1) corresponds to a diameter of the hole (32) in the dental model (3).

Figure 9:
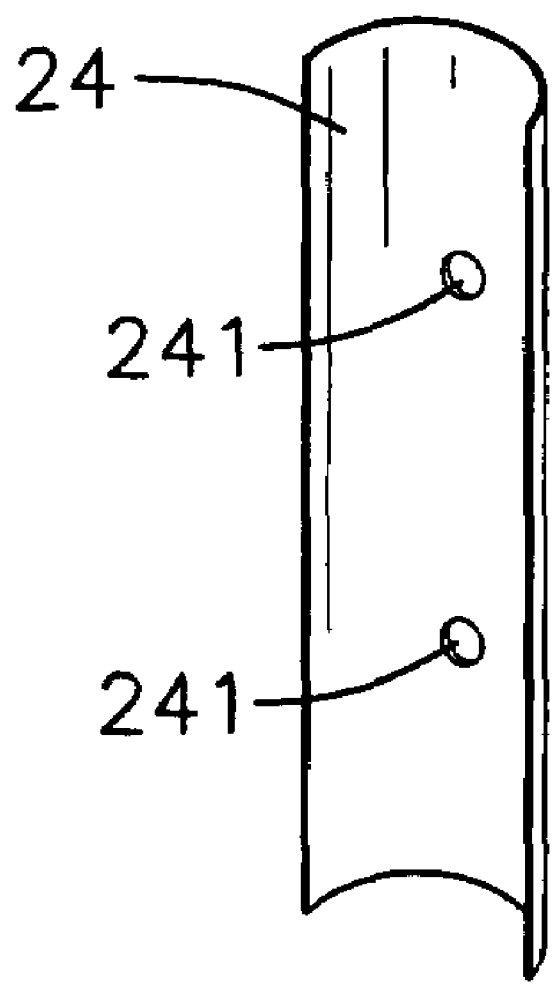
FIG. 9 is a perspective view of a fourth guide of the positioning device in FIG. 1 with multiple holes.
Figure 10:
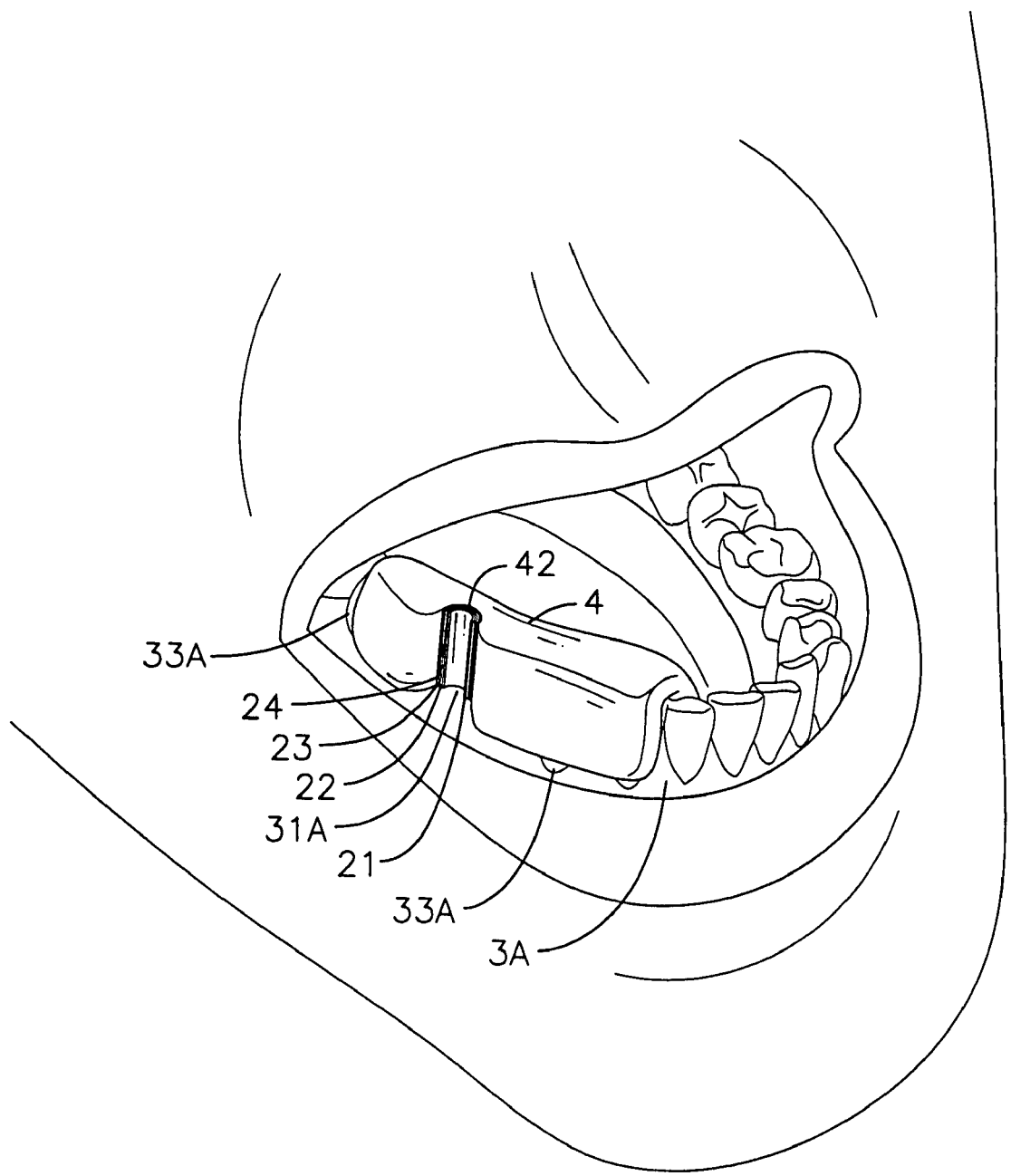
FIG. 10 is an operational perspective view of the resin guide bridge with the guides of the positioning device put on a patient's jaw bone.
Figure 11:
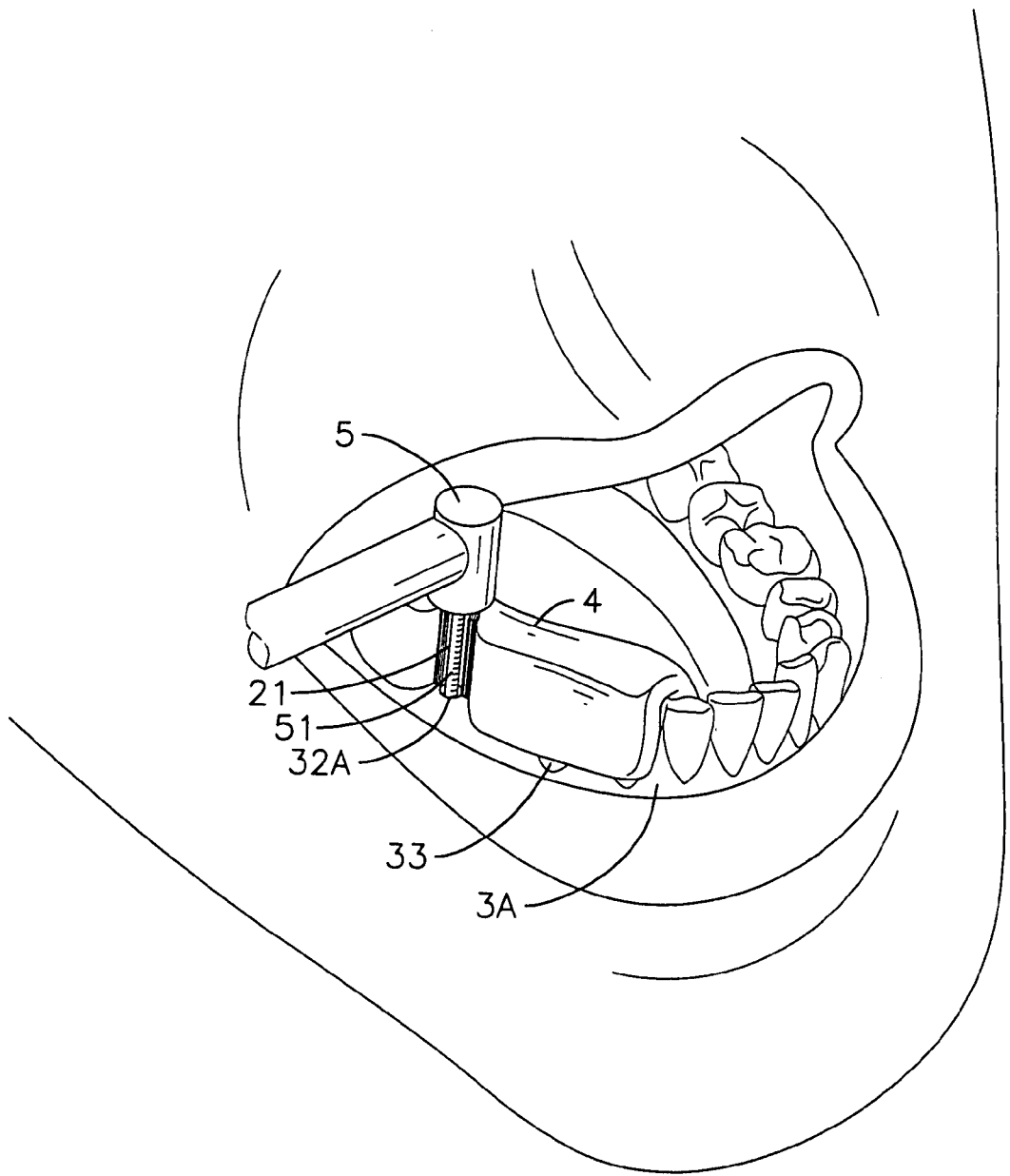
FIG. 11 is an operational perspective view of a drilling device drilling a bone cavity in a patient's jaw bone in FIG. 10 through the first guide of the positioning device on the resin guide bridge.
Figure 12:
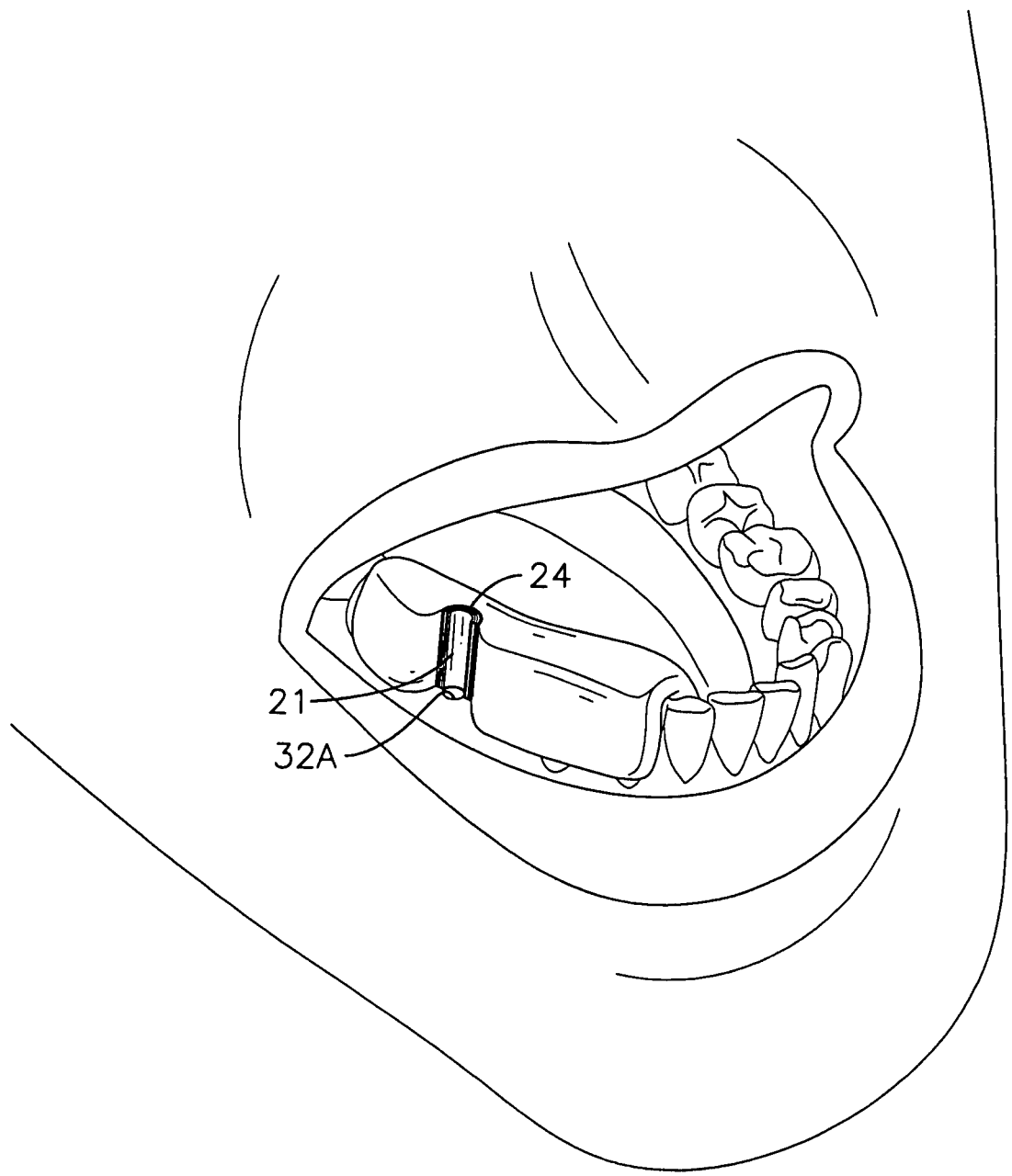
FIG. 12 is an operational perspective view of the patient's jaw bone with the finished bone cavity corresponding the first guide of the positioning device in FIG. 11.
Figure 13:
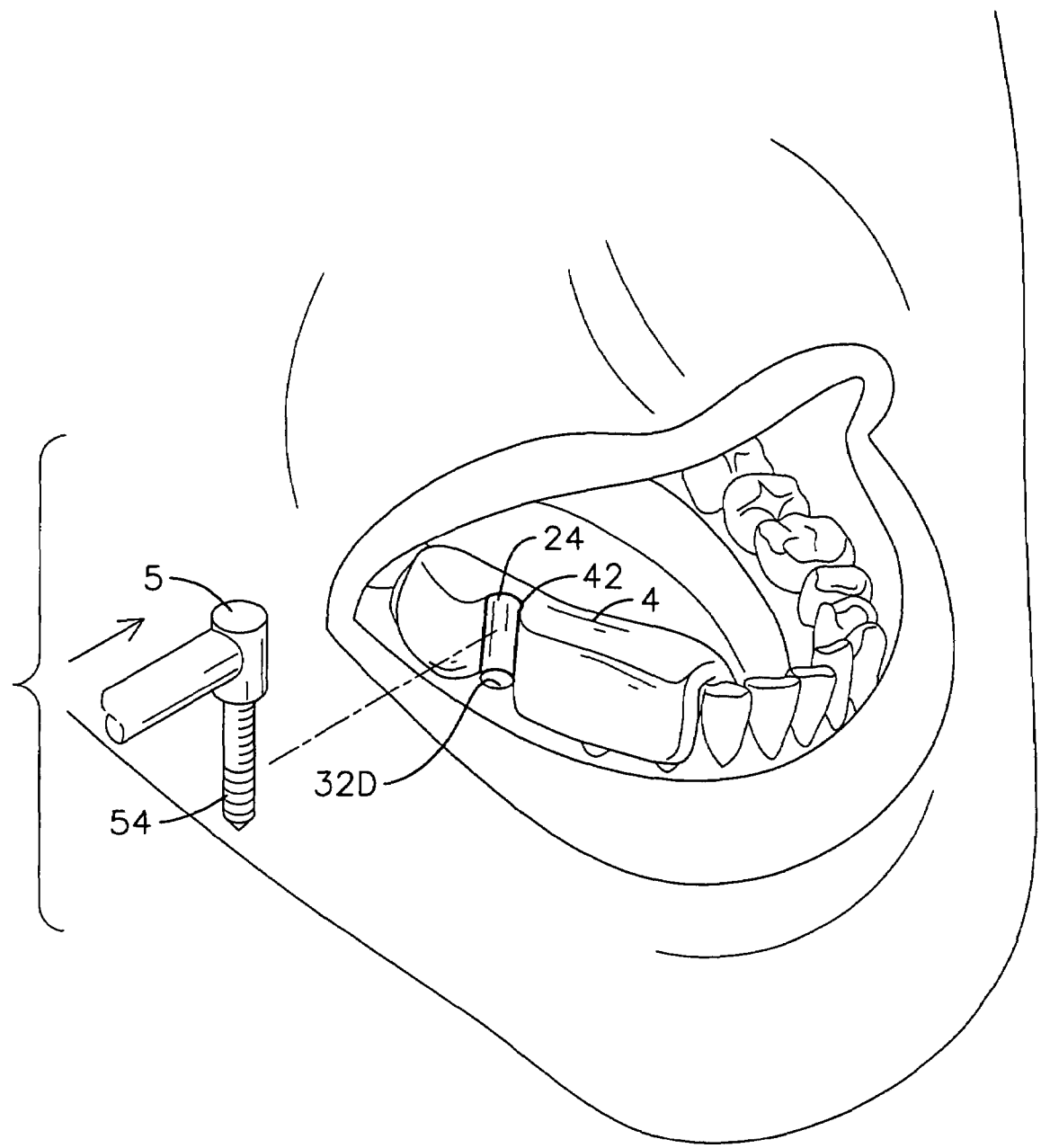
FIG. 13 is an operational perspective view of the drilling device enlarging the bone cavity on a patient's jaw bone through a fourth guide of the positioning device in FIG. 10.

The guides (21, 22, 23, 24) are semi-tubular tabs, made of magnetic material and each guide(21, 22, 23, 24) comprises an inner concave, an inner diameter and an outer diameter. The guides (21, 22, 23, 24) are mounted detachably on the post (1) concentrically abuts one another according to their sizes. The inner diameter of an innermost guide (21) corresponds to the diameter of the post (1). The outer diameter of an inner one of any adjacent two of the guides (21, 22, 23, 24) corresponds to the inner diameter of an outer one of the adjacent two of the guides (21, 22, 23, 24). An outermost guide (24) may have at least one mounting hole (241) transversely defined through the outermost guide (24) as shown in FIG. 9.

In a preferred embodiment, the guides (21, 22, 23, 24) may have a first guide (21), a second guide (22), a third guide (23) and a fourth guide (24).

Figure 3:
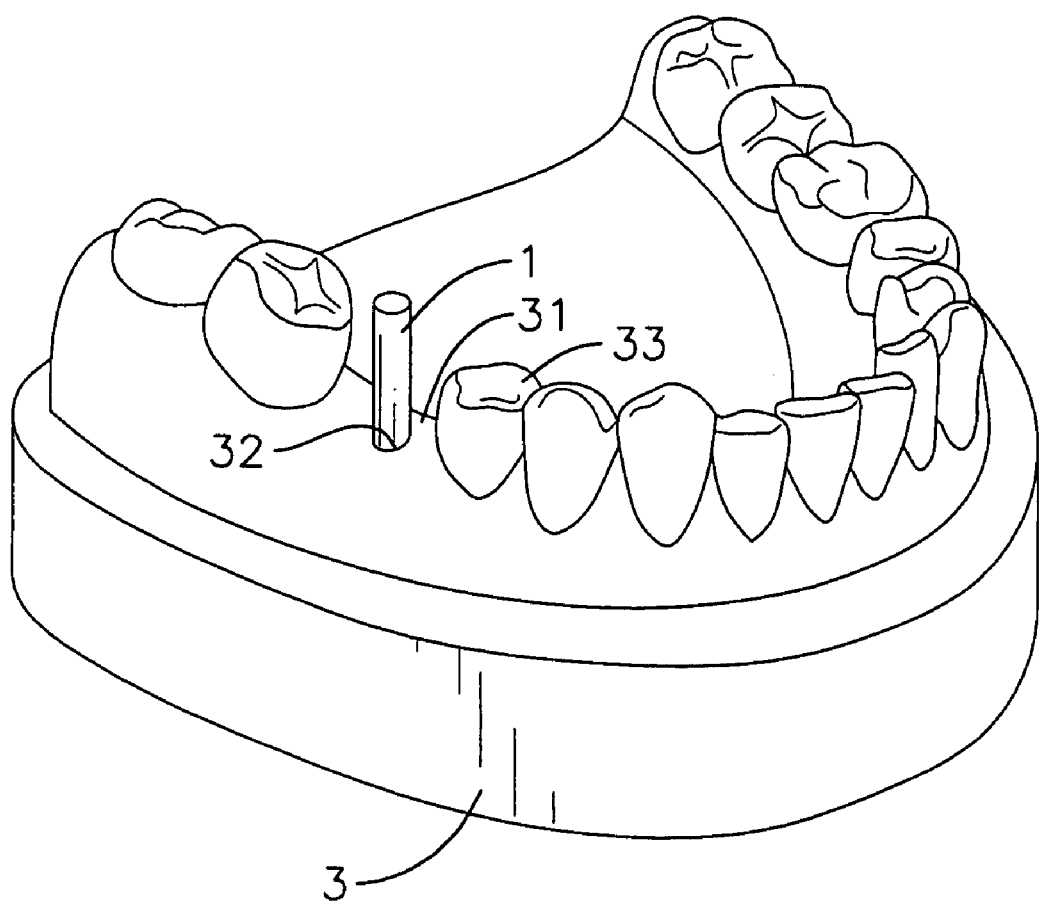
FIG. 3 is an operational perspective view of the dental model with a post of the positioning device in FIG. 1 inserted into the hole in FIG. 2.
Figure 4:
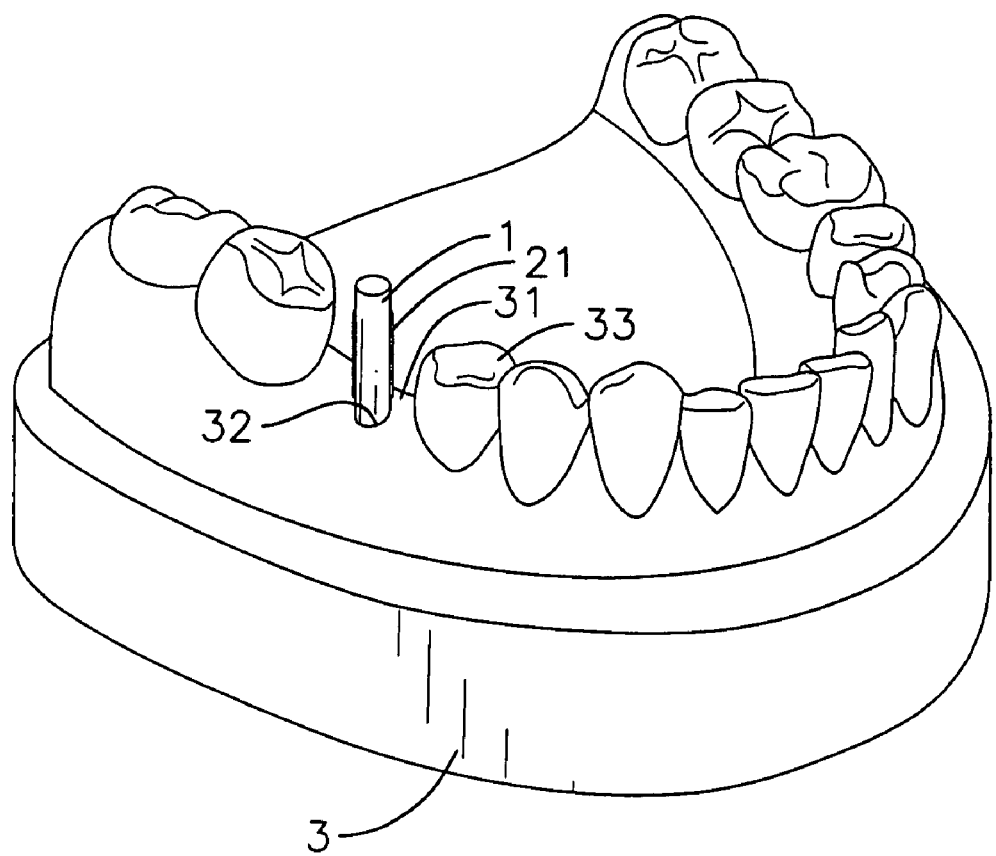
FIG. 4 is an operational perspective view of a first guide attached to the post of the positioning device on the dental model in FIG. 3.
Figure 5:
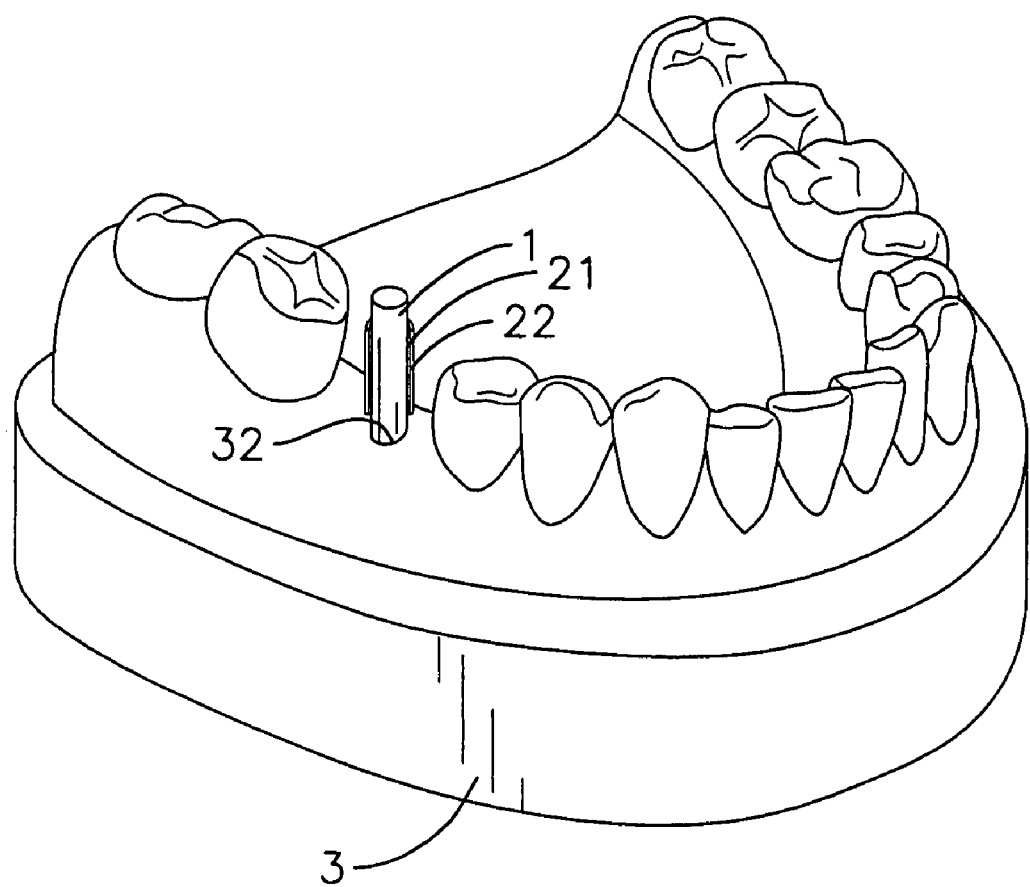
FIG. 5 is an operational perspective view of a second guide attached to the first guide of the positioning device in FIG. 4.
Figure 6:
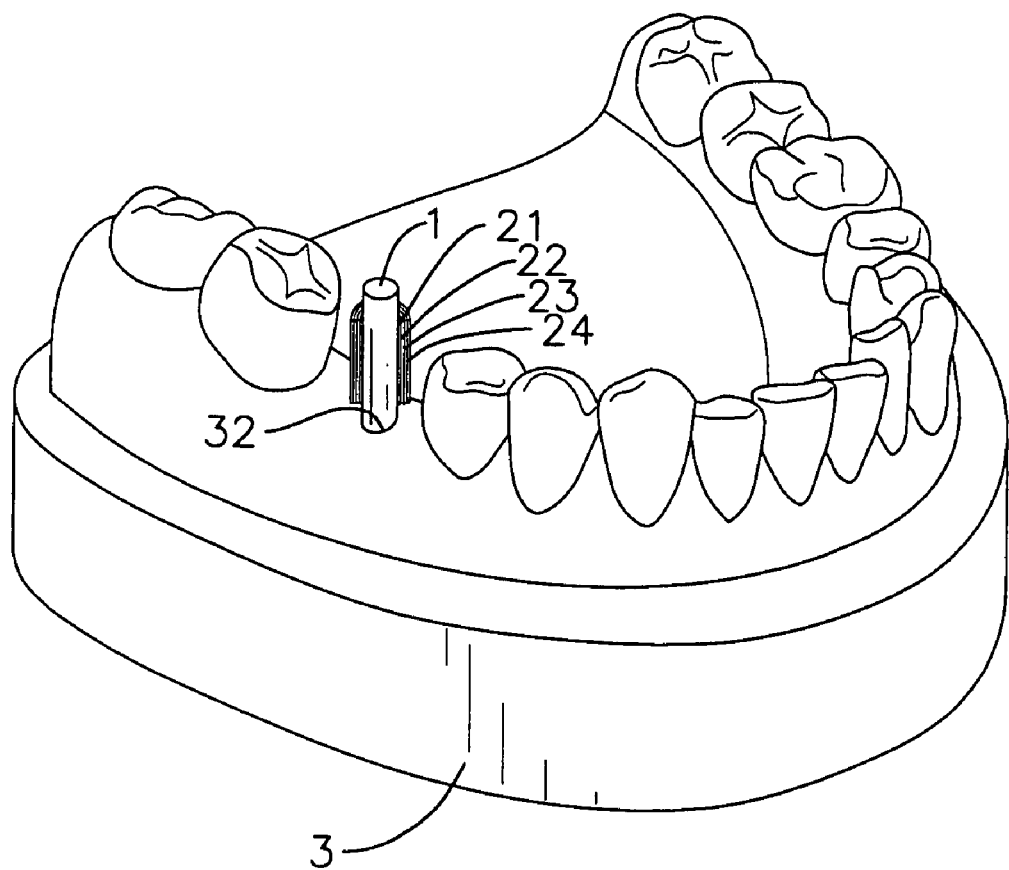
FIG. 6 is an operational perspective view of a third guide and a fourth guide attached sequentially to the second guide of the positioning device in FIG. 5.

With reference to FIGS. 2 and 3, a dental implantation is implemented with the positioning device. A dentist drills the hole (32) in an edentulous place (31) of the dental model (3) and inserts the post (1) into the hole (32). With further reference to FIGS. 4 to 6, the post (1) is inserted into the hole (32) and the first guide (21) is attached to the post (1) so the inner concave of the first guide (21) faces outside the dental model (3). After positioning the first guide (21), the second guide (22) is attached to the first guide (21), the third guide (23) is attached to the second guide (22) and so on. Number of the guides (21, 22, 23, 24) matches number of times that a bone cavity in a patient's jaw bone is drilled.

Figure 7:
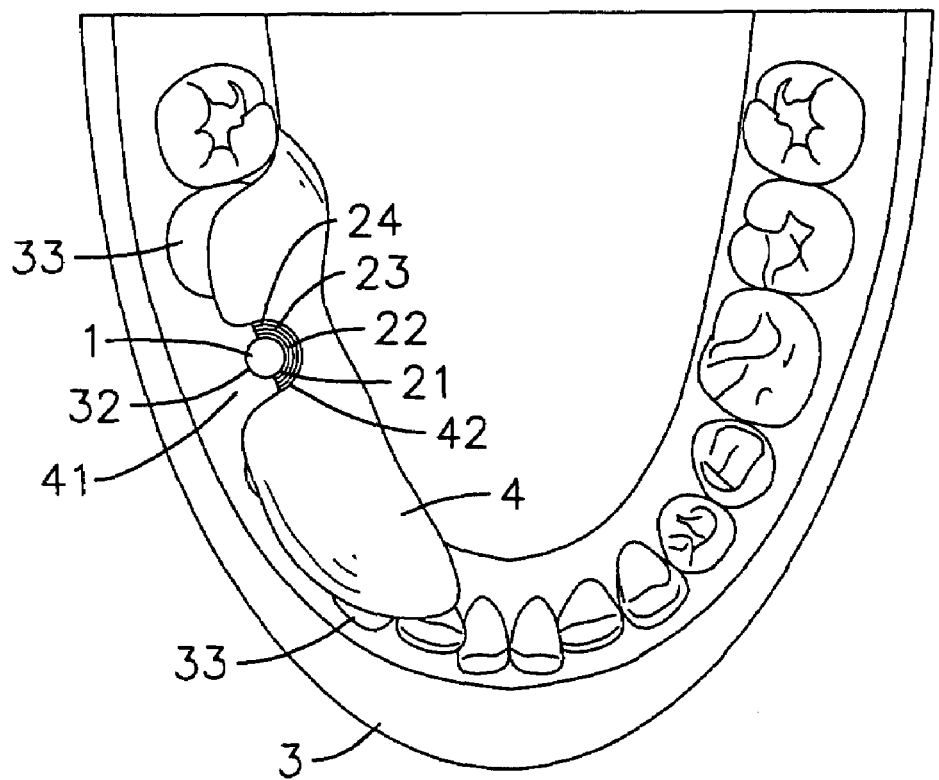
FIG. 7 is a top view of the dental model coated with resin adjacent to the guides of the positioning device to form a resin guide bridge in FIG. 6.
Figure 8:
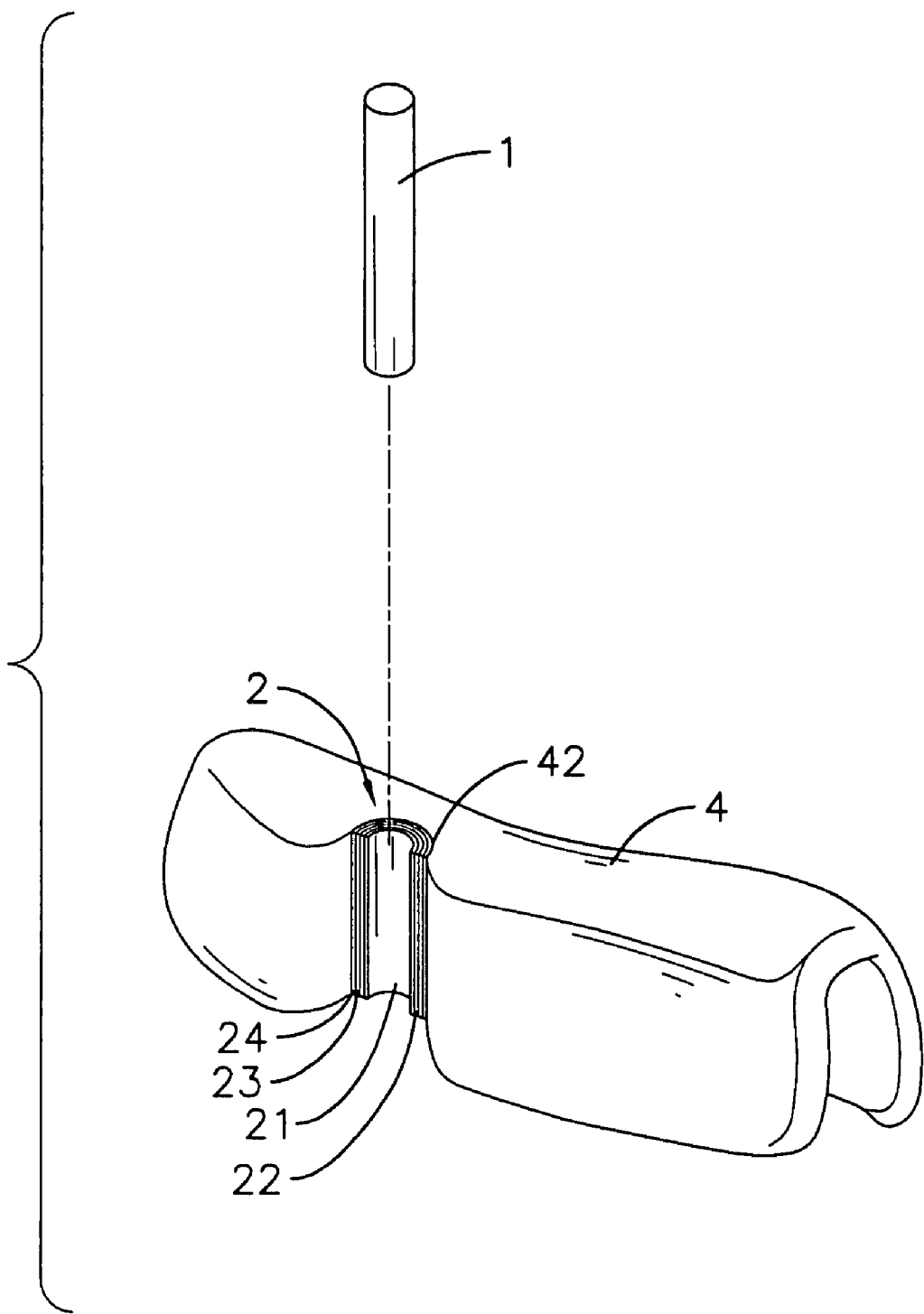
FIG. 8 is an operational perspective view of the resin guide bridge and the positioning device in FIG. 7 with the post removed.

With reference to FIGS. 7 and 8, wax or gypsum is filled in gaps between the teeth and grooves over the occlusal surface. Then, the dental model (3) is coated with resin on the edentulous place (31) and the teeth thereof to form a resin guide bridge (4) with an outside recess (41) which the post (1), the first guide (21), the second guide (22), the third guide (23) and the fourth guide (24) correspond to. After the resin is setting, a semi-tubular surface (42) is formed on the resin guide bridge (4) and corresponds to the post (1) with the guides (21, 22, 23, 24). The semi-tubular surface (42) can be coated with viscose to stick to the fourth guide (24) or bonded through the retention holes. With further reference to FIG. 9, the partially resin is filled into the mounting holes (241) in the fourth guide (24) so that the resin guide bridge (4) is combined securely with the fourth guide (24). Then the post (1) is removed from the resin guide bridge (4).

With reference to FIGS. 10 to 13, the resin guide bridge (4) with the first guide (21), the second guide (22), the third guide (23) and the fourth guide (24) puts on an edentulous place (31A) and adjacent teeth over the jaw bone (3A). Because an inner surface of the resin guide bridge (4) corresponds to the edentulous place (31A) and the teeth thereof, the first guide (21) precisely points to a target on the jaw bone (3A) which will be drilled later. A dentist can drill the jaw bone (3A) along the first guide (21) to form the first bone cavity (32A) by a drilling device (5) with a first drill bit (51). Then the dentist removes the first guide (21) to expose the second guide (22) and drills and enlarges the bone cavity (3A) along the second guide (22) by an second drill bit having a diameter larger than that of the first drill bit (51). The dentist repetitively drills the bone cavity (32A) with different drill bits having increased diameters until the bone cavity (32D) is great enough to receive the dental implant (64A).

Another dental implantation with the positioning device is described hereinafter.

Figure 14:
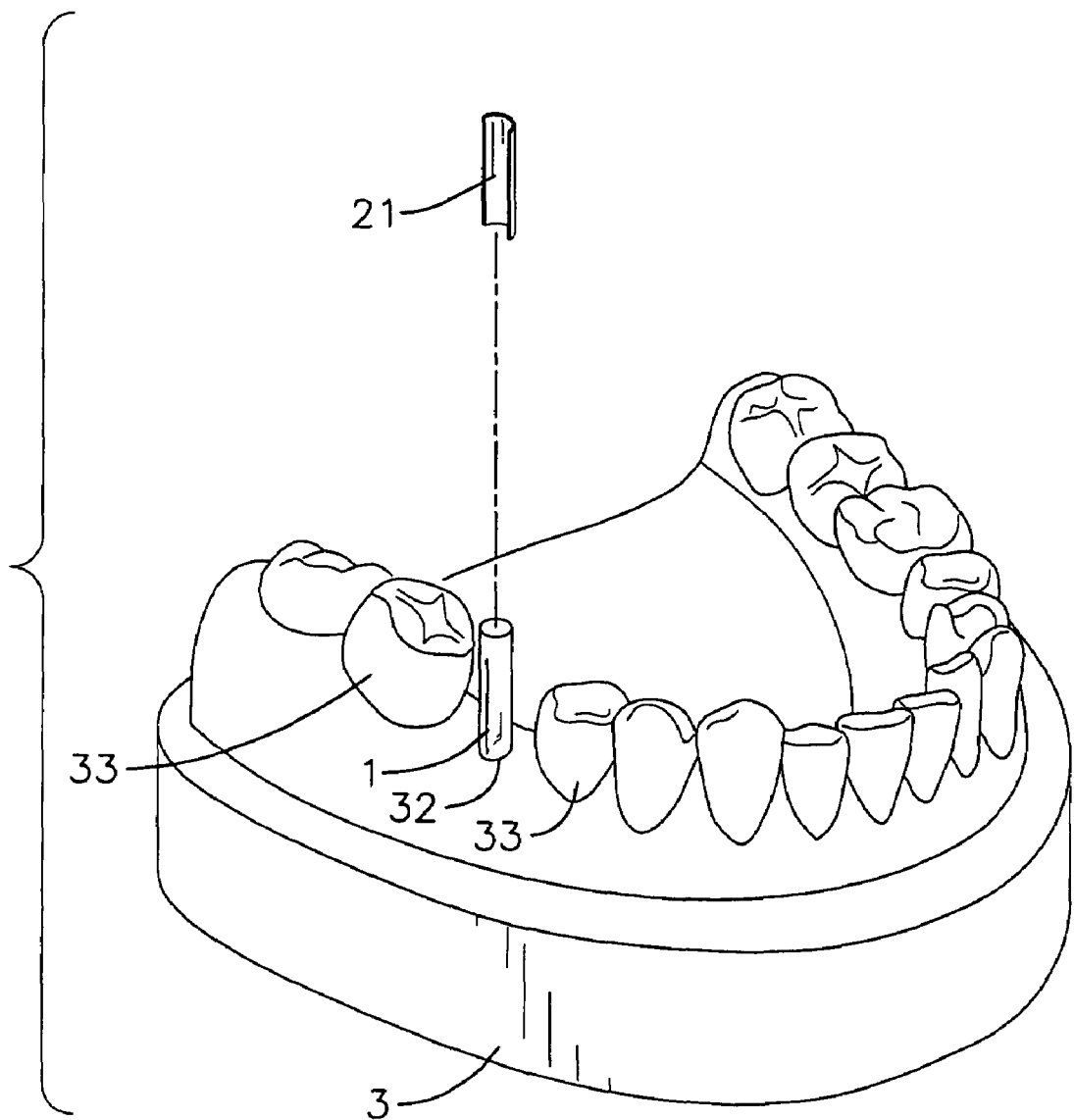
FIG. 14 is an exploded perspective view of a first guide attached to the post of the positioning device in FIG. 4.

With reference to FIG. 14, the dentist drills the hole (32) in the edentulous place (31) in the dental model and inserts the post (1) into the hole (32). The first guide (21) is attached to the post (1) with the inner concave of the first guide (21) facing outside the dental model (3).

Figure 15:
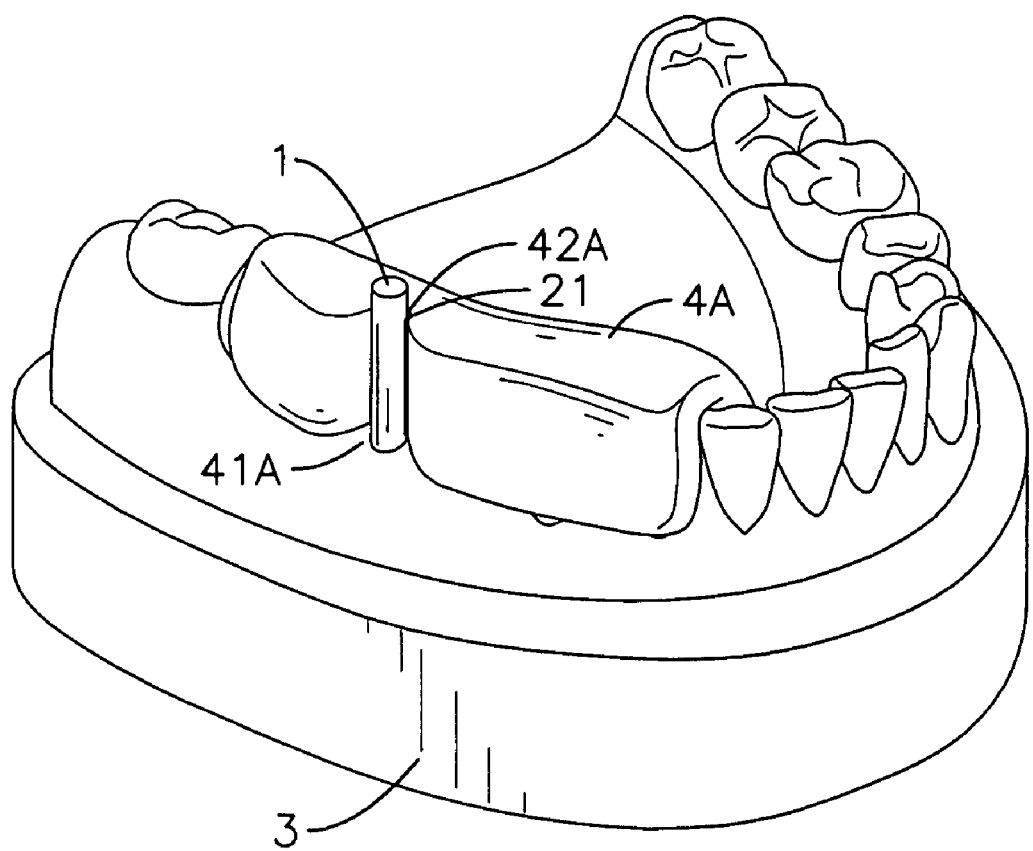
FIG. 15 is an operational perspective view of the dental model coated with resin in FIG. 14 adjacent to the first guide of the positioning device to form a first resin guide bridge.
Figure 16:
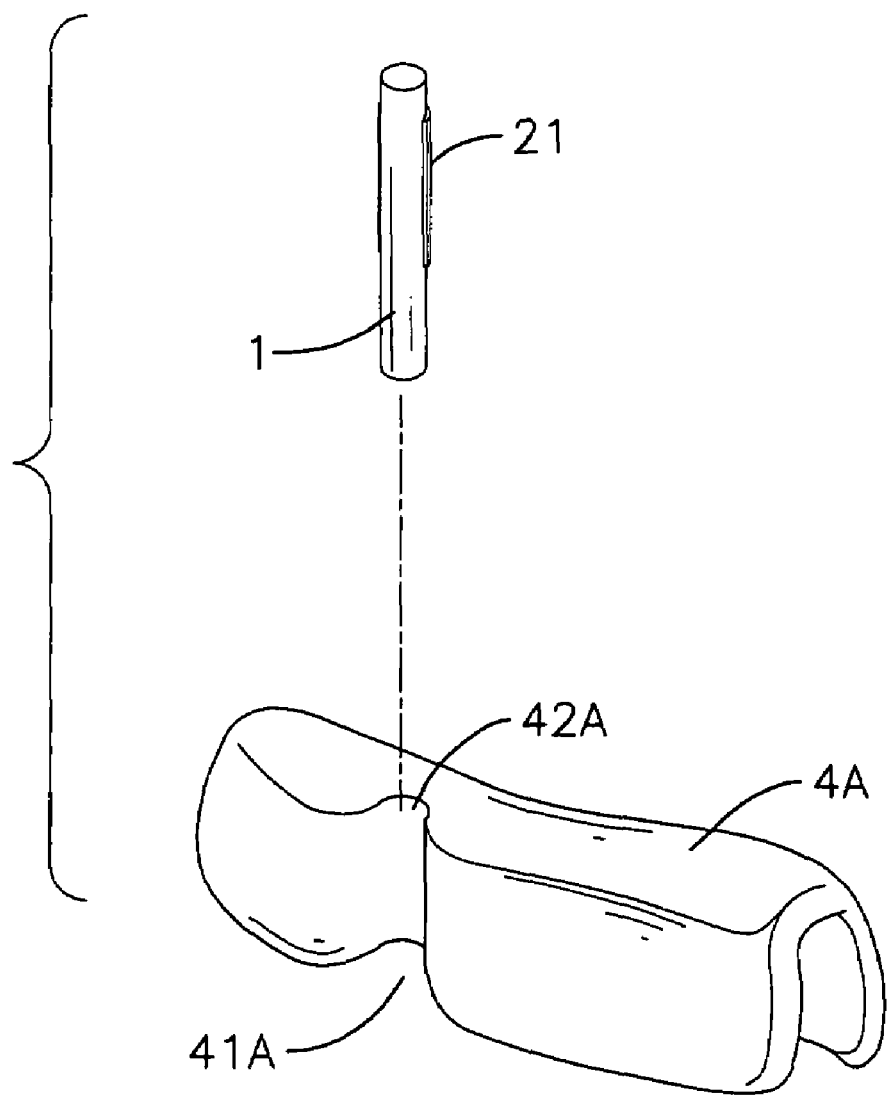
FIG. 16 is an operational perspective view of the resin guide bridge separating from the post and the first guide of the positioning device in FIG. 15.

With reference to FIGS. 15 and 16, wax or gypsum is filled into the gap of the teeth. Then the dental model (3) is coated with resin on the edentulous place (33) and the teeth of the dental model (3) to form a first resin guide bridge (4A) with an outside recess (41A) corresponding to the post (1) and the first guide (21). After the resin hardens, a semi-tubular surface is formed on the first resin guide bridge (4A) and corresponds to the post (1) and the first guide (21). Then the dentist takes the first resin guide bridge (4A) away from the dental model (3) and removes the post (1) and the first guide (21) from the first resin guide bridge (4A).

Figure 17:
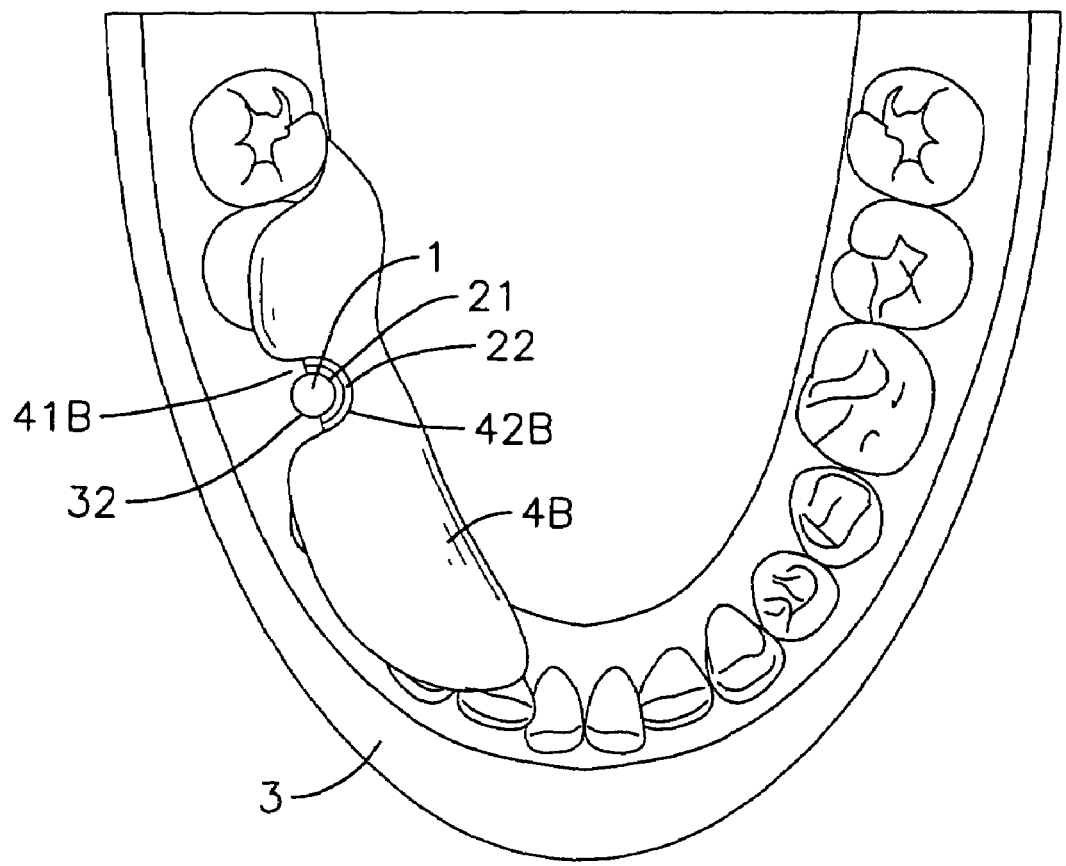
FIG. 17 is an operational top view of the dental model coated with resin adjacent to the second guide of the positioning device to form a second resin guide bridge.
Figure 18:
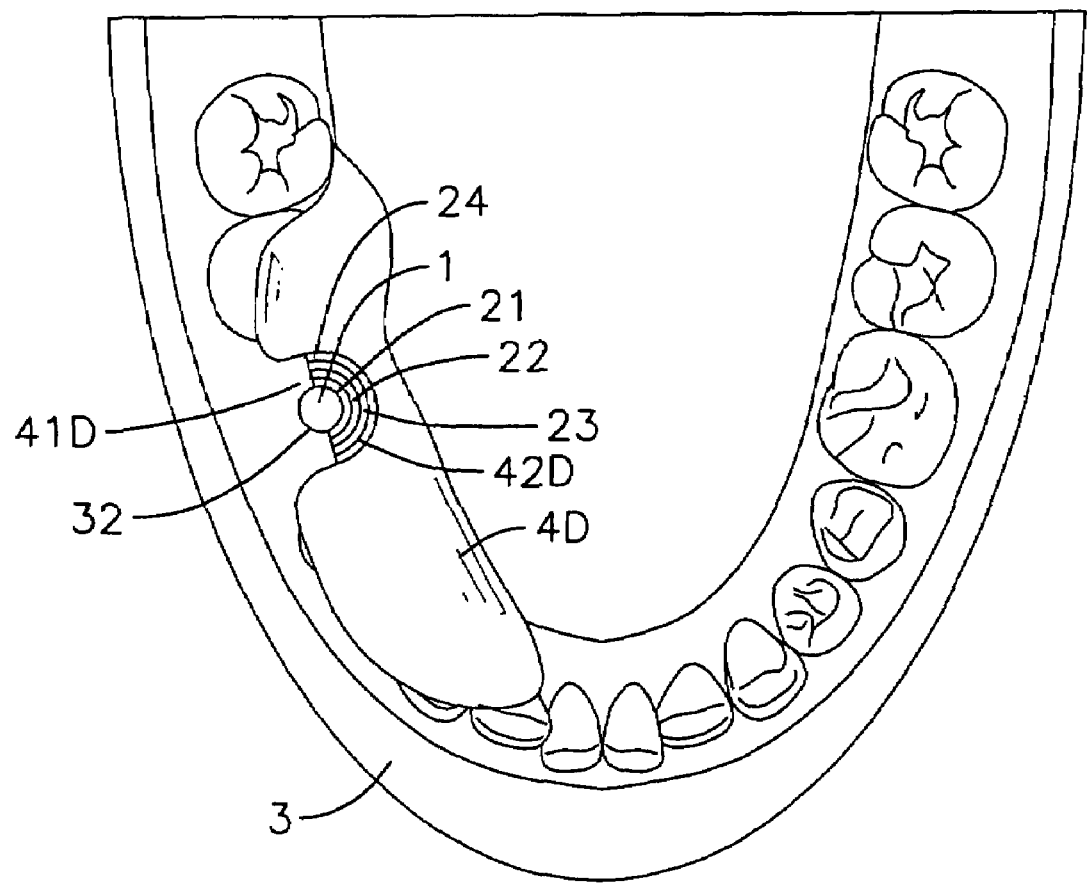
FIG. 18 is an operational perspective view of the dental model coated with resin adjacent to the fourth guides to form a fourth resin guide bridge.

With further reference to FIGS. 17 and 18, the post (1) with the first guide (21) inserts into the hole (32) again. The second guide (22) is attached to the first guide (21) to manufacture a second resin guide bridge (4B) by the same means used to manufacture the first resin guide bridge (4A). Then the first guide (21), the second guide (22), the third guide (23) and the fourth guide (24) are mounted respectively in corresponding resin guide bridges (4A, 4B, 4D).

Figure 19:
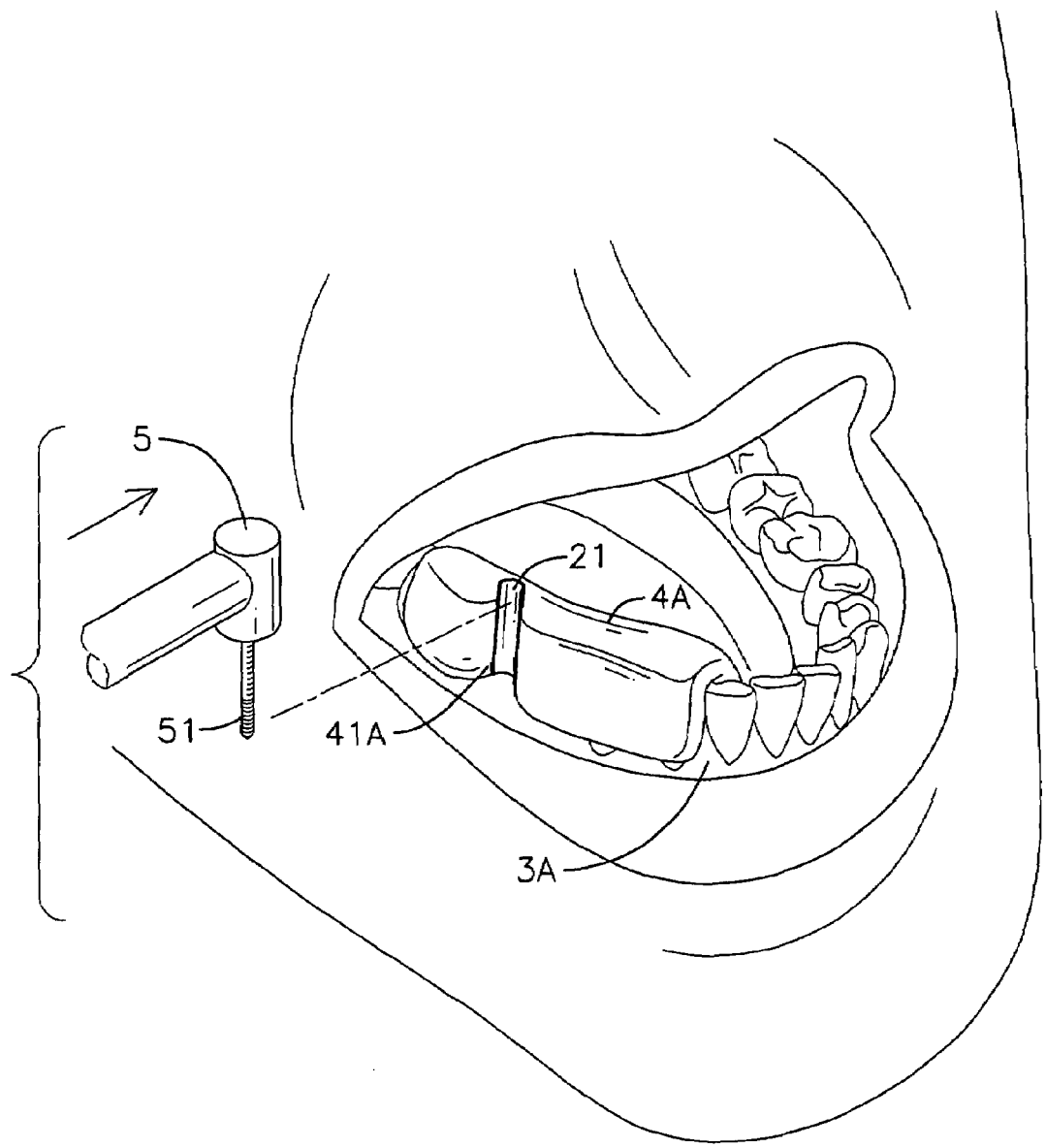
FIG. 19 is an operational exploded perspective view of a drilling device drilling a bone cavity on a patient's jaw bone through the first guide of the positioning device.
Figure 20:
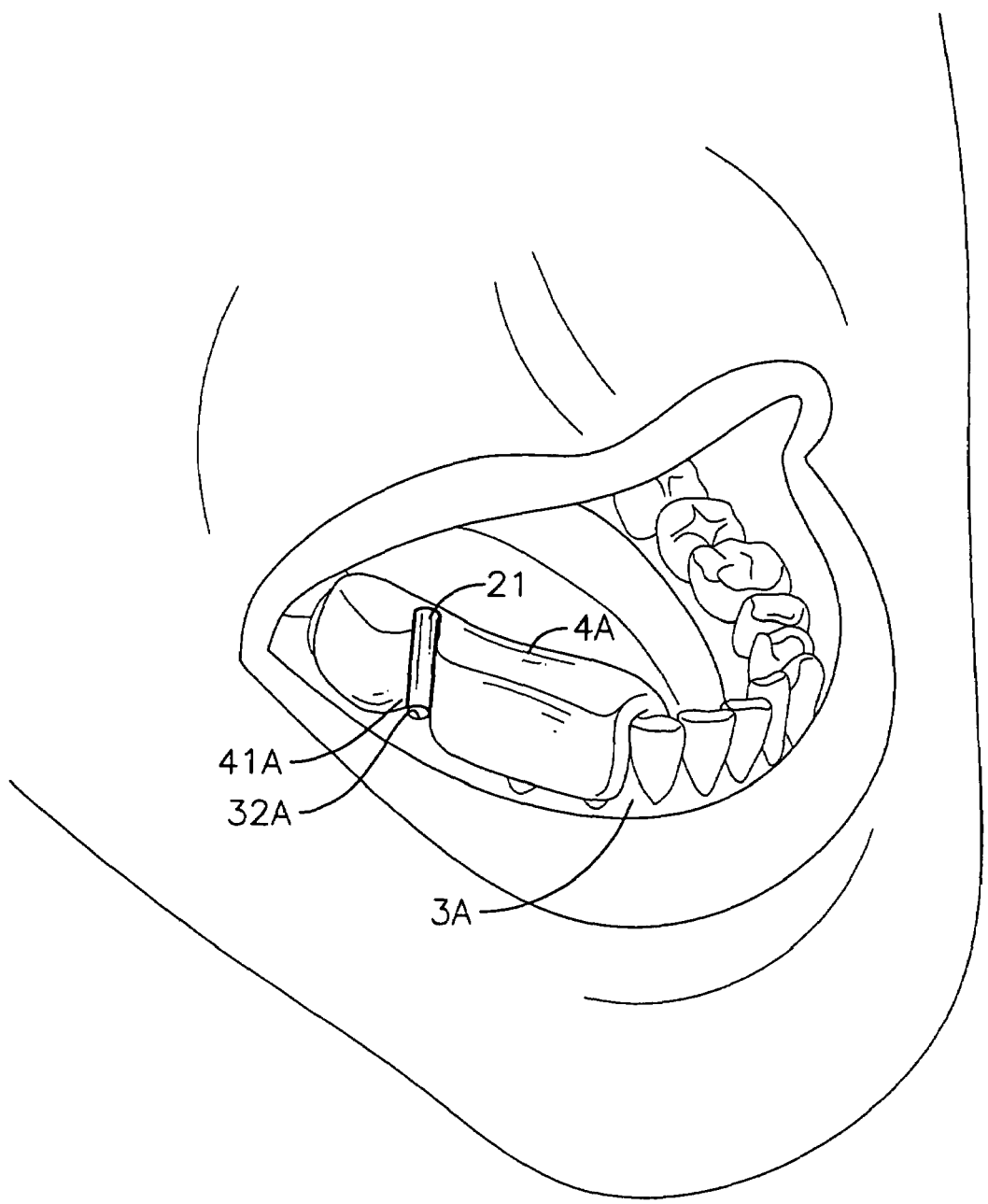
FIG. 20 is an operational perspective view of the patient's jaw bone with the finished bone cavity corresponding to the first guide of the positioning device in FIG. 19.
Figure 21:
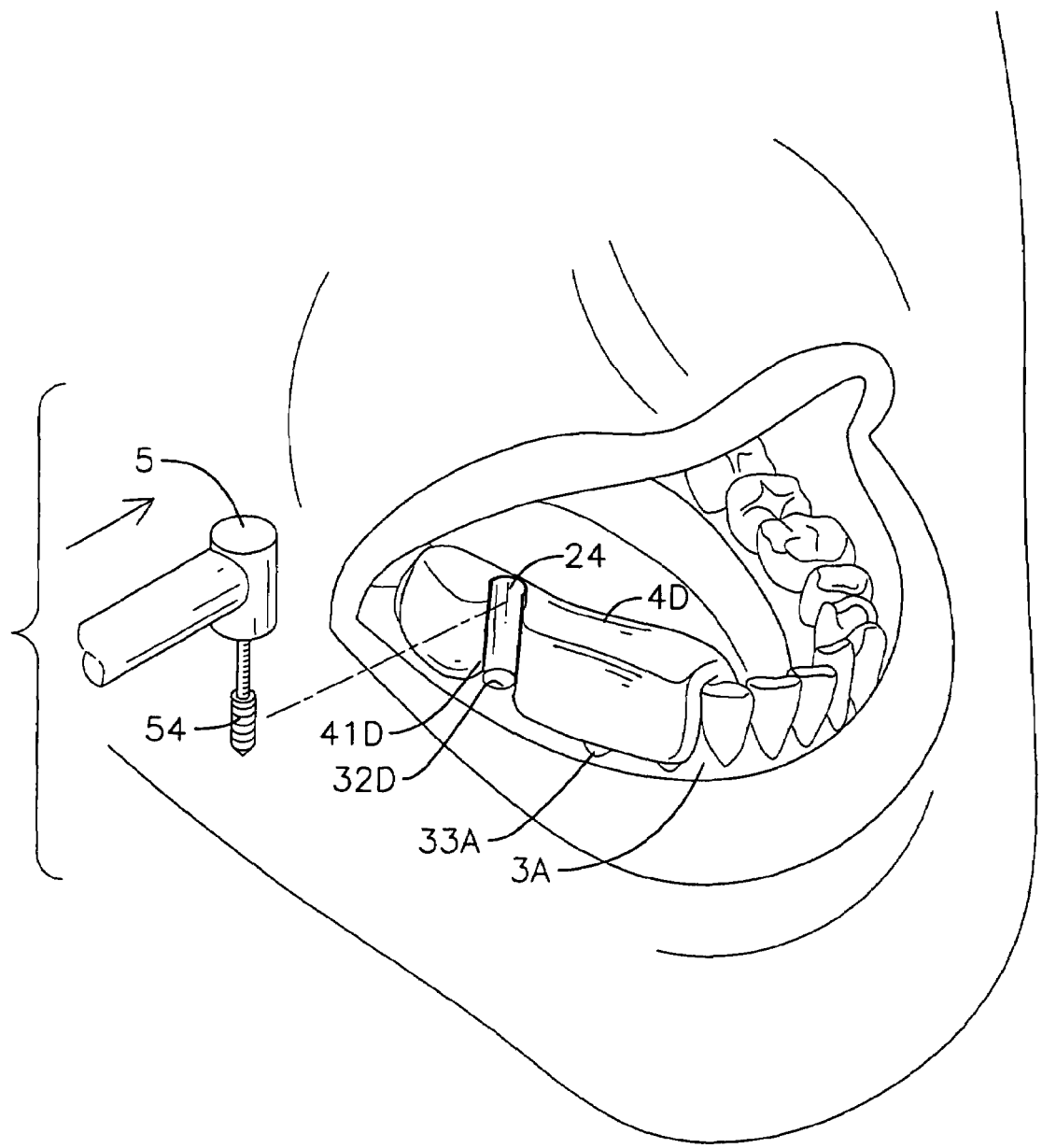
FIG. 21 is an operational perspective view of the drilling device enlarging the bone cavity on a patient's jaw bone in FIG. 20 through the fourth guide of the positioning device.
Figure 22:
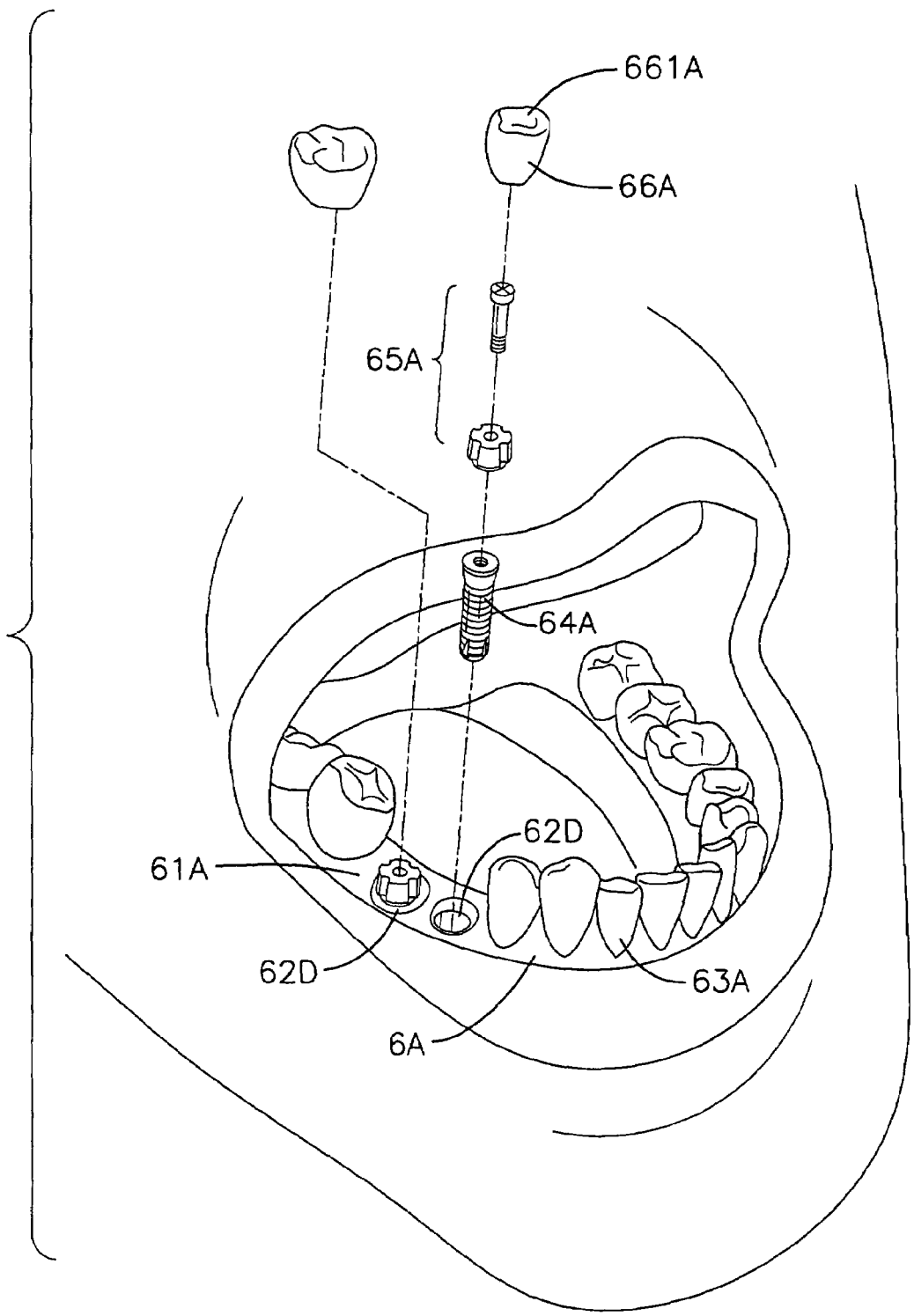
FIG. 22 is an operational exploded perspective view of a patient's jaw bone with dental implants in accordance with the prior art.
Figure 23:
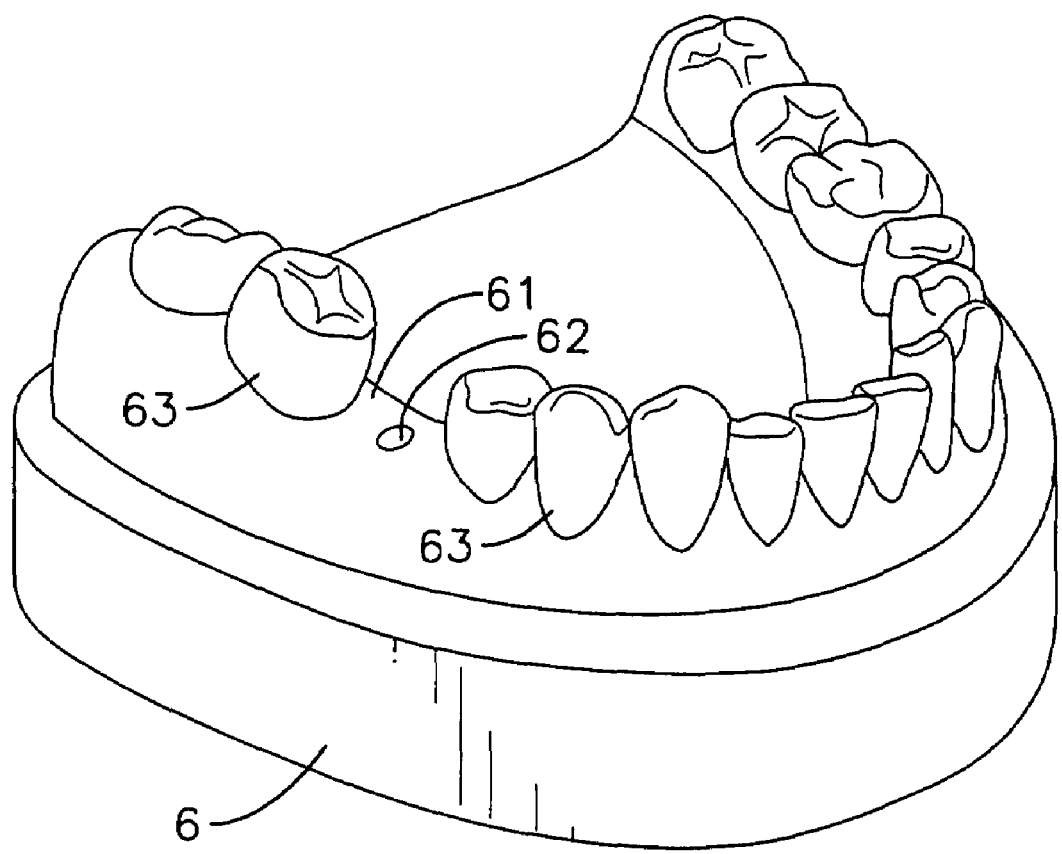
FIG. 23 is a perspective view of a dental model with first hole.
Figure 24:
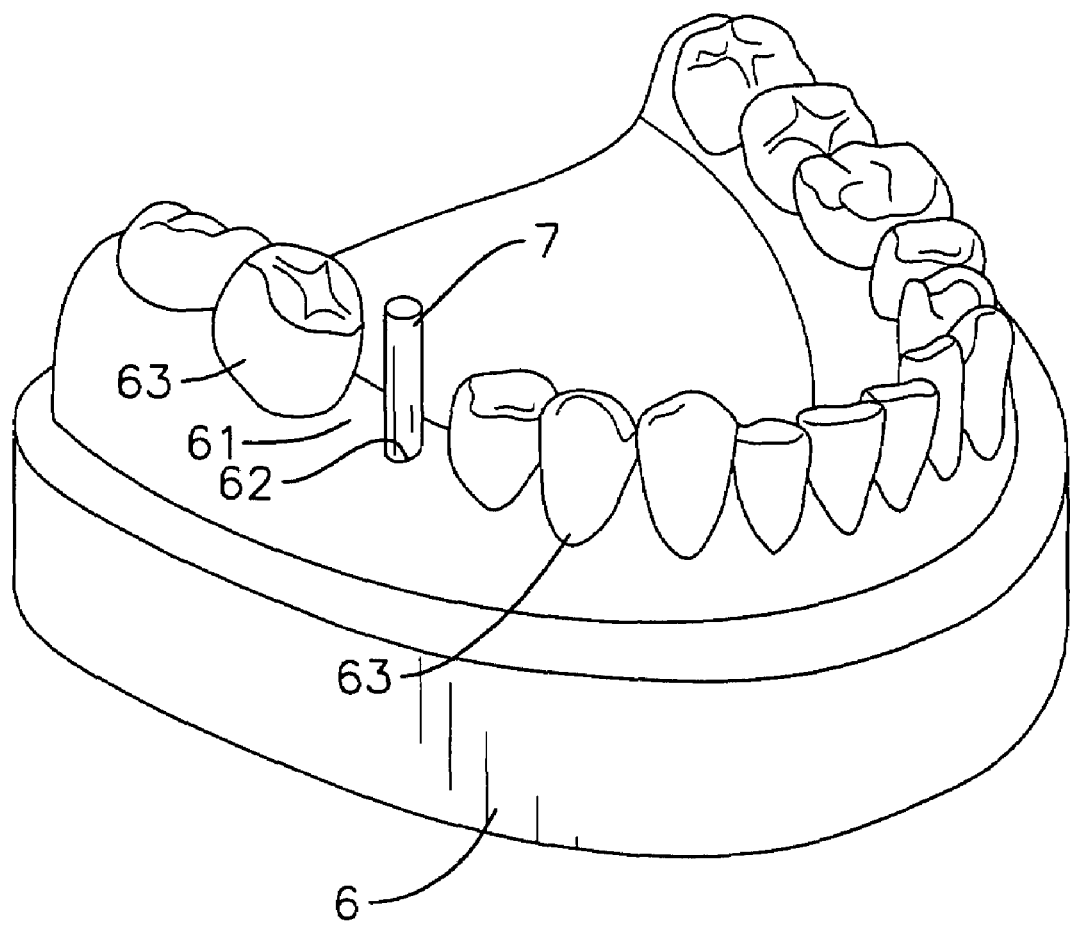
FIG. 24 is a perspective view of the dental model with a post inserted into the hole in FIG. 23.
Figure 25:
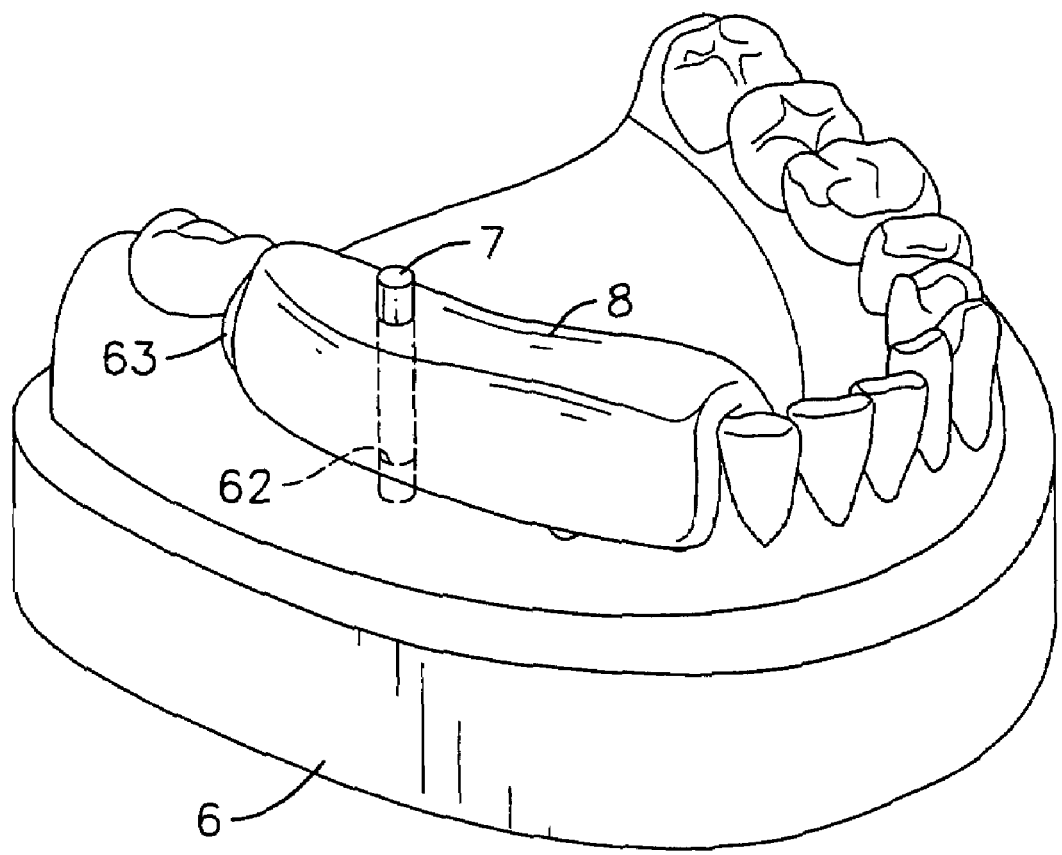
FIG. 25 is a perspective view of the dental model in FIG. 24; coated with resin to form a first resin guide bridge.
Figure 26:
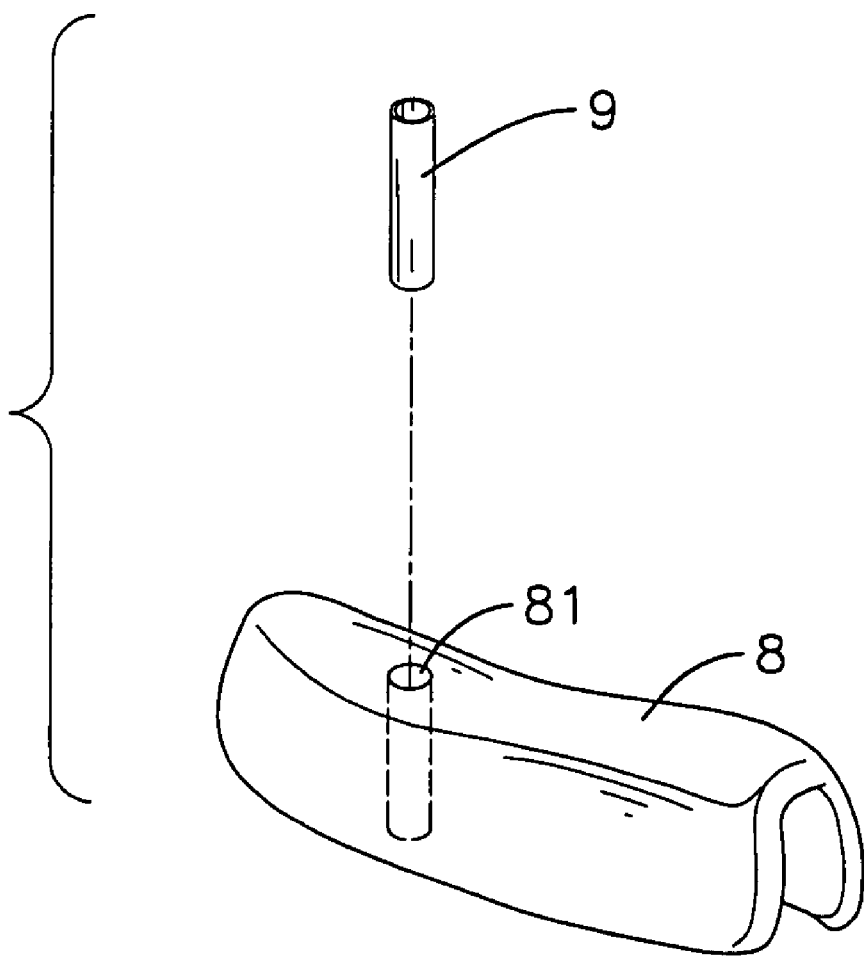
FIG. 26 is an exploded perspective view of a first placement resin guide bridge with a first guide tube.
Figure 27:
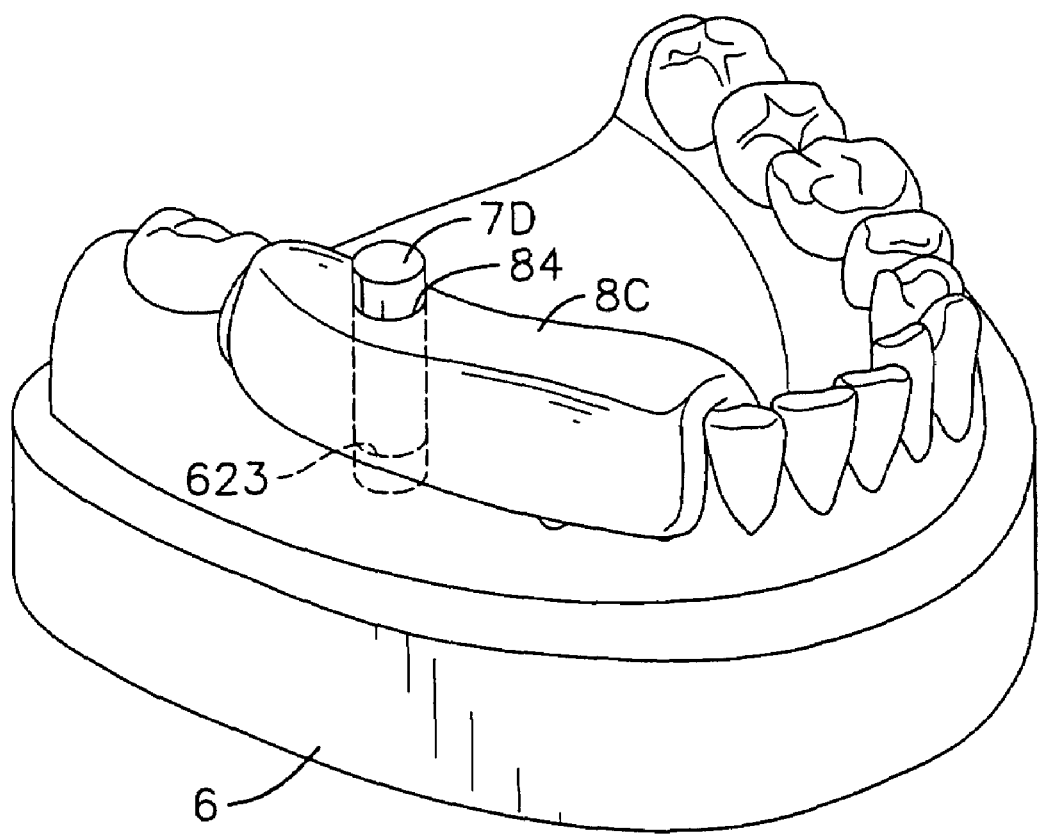
FIG. 27 is a perspective view of the dental model in FIG. 24 coated with resin to form a fourth resin guide bridge.
Figure 28:
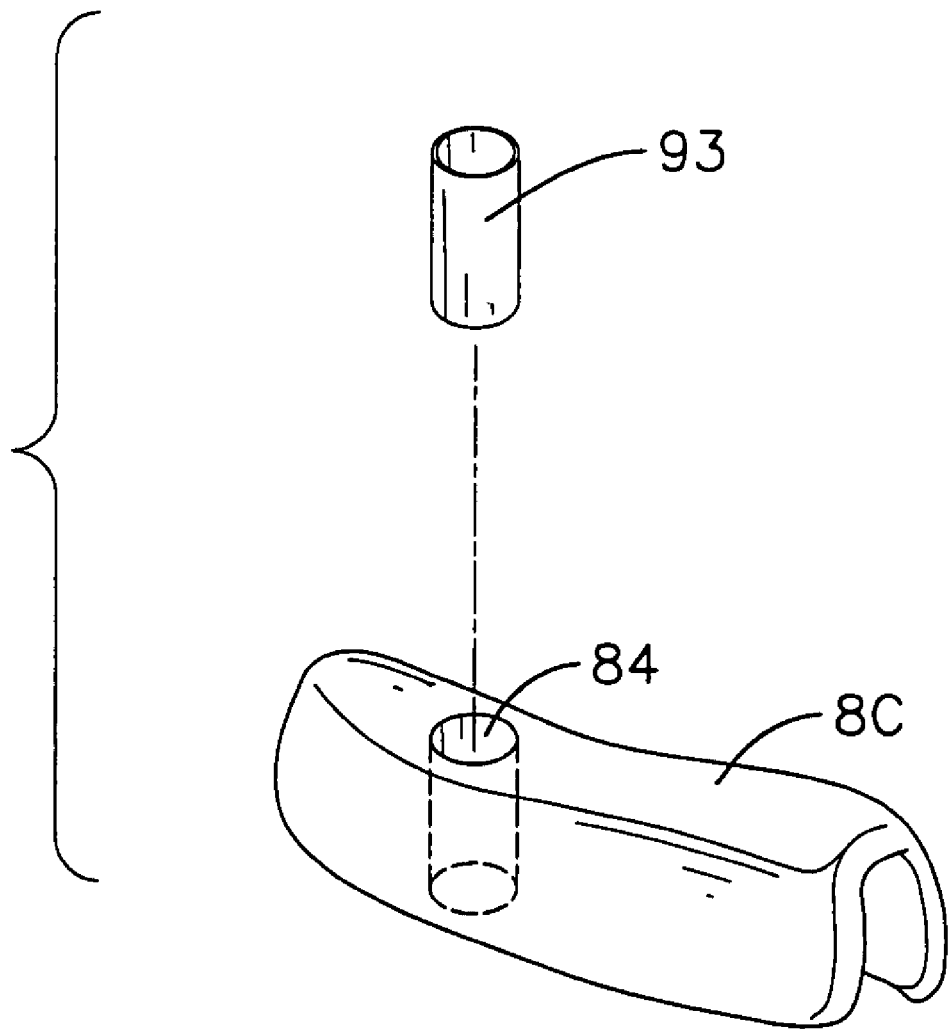
FIG. 28 is an exploded perspective view of the fourth resin guide bridge and a fourth guide tube.
Figure 29:
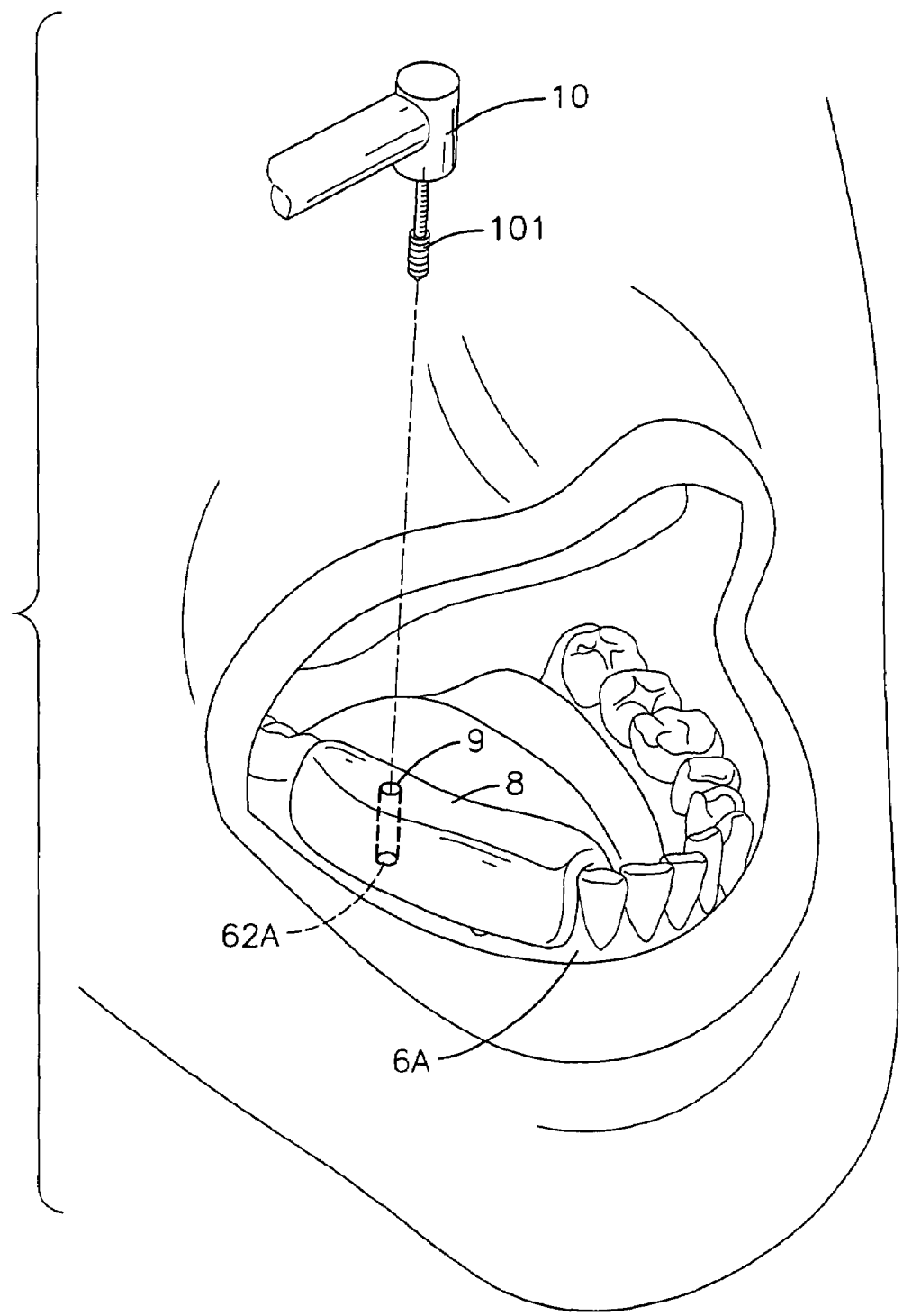
FIG. 29 is an operational perspective view of the first resin guide bridge put on a patient's jaw bone in FIG. 22.
Figure 30:
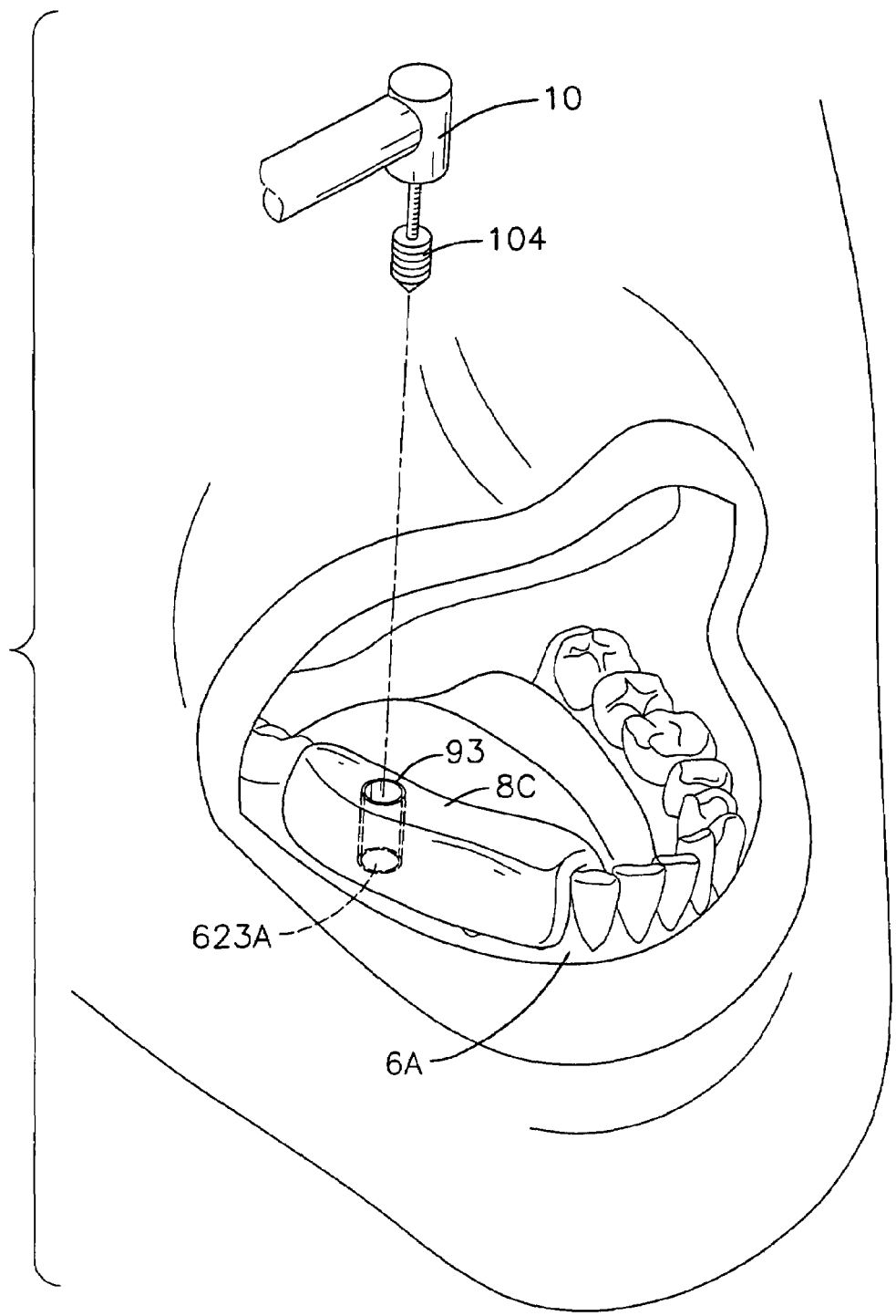
FIG. 30 is an operational perspective view of the fourth resin guide bridge put on a patient's jaw bone in FIG. 29.
Figure 31:
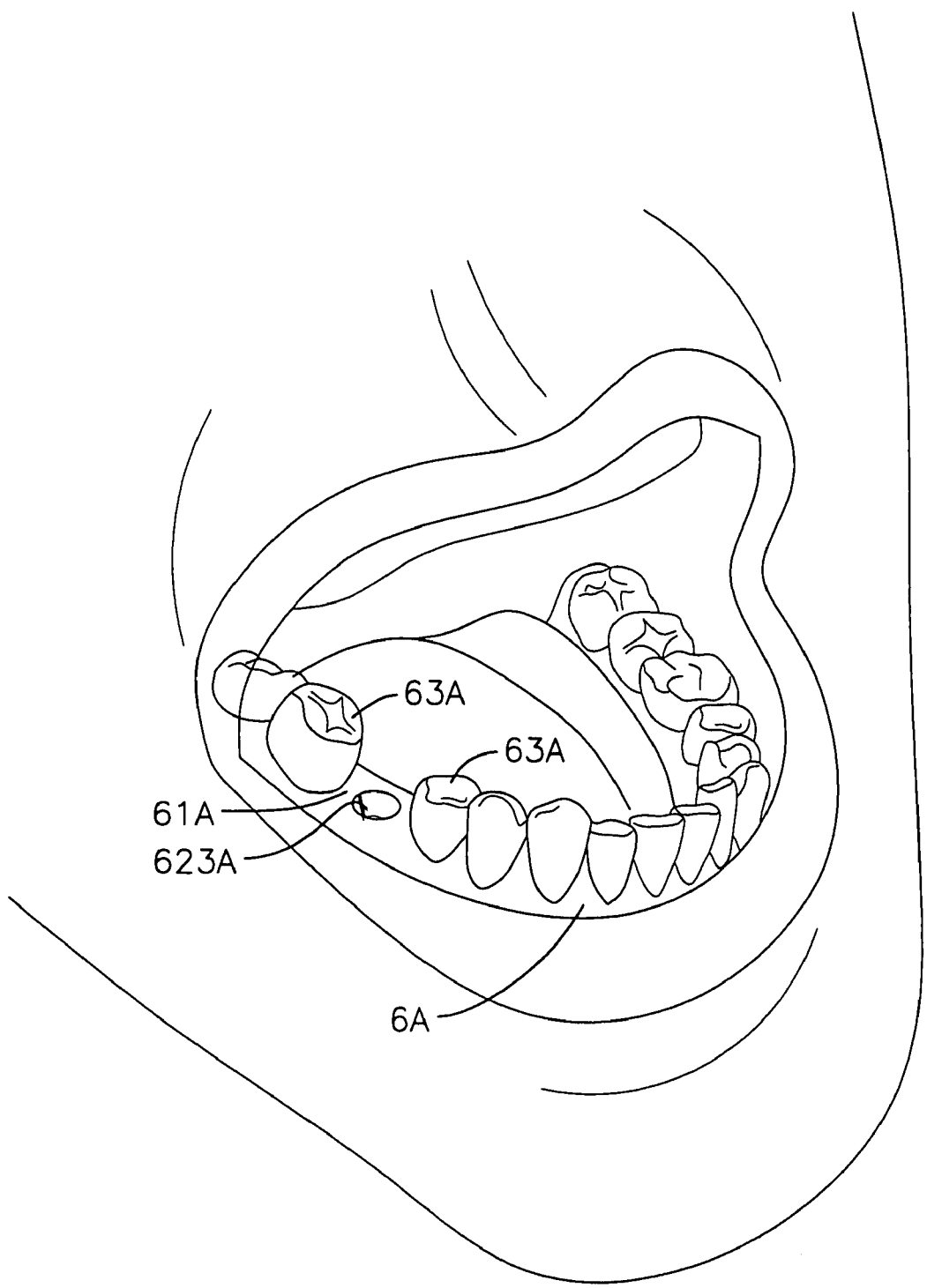
FIG. 31 is an operational perspective view of the patient's jaw bone in FIG. 30 with the finished bone cavity.

With reference to FIGS. 19 to 21, the dentist puts the first resin guide bridge (4A) with the first guide (21) on the patient's jaw bone (3A) and drill the bone cavity (32A). The dentist repetitively drills and enlarges the bone cavity (32A) by replacing the resin guide bridge (4B, 4D) and the drill bit until the bone cavity (32D) is great enough to receive the dental implant (64A).

The present invention has following advantages:

1. The drill bit of the drilling device can horizontally move into the outside recess to drill a bone cavity according to the guides. Therefore, the drill needn't move over the resin guide bridge to drill a bone cavity according to the guides. So a patient with a small mouth or being treated in the posterior place does not have to excessively open his mouth when experiencing the dental implantation. Therefore, the patient suffers less pain and pressure during the period of the dental implantation.

2. The dentist can directly look at the drill bit in the outside recess to identify the depth of the bone cavity.

3. Manufacture of the resin guide bridge is simple because the dentist needn't repeatedly drill the holes and insert the different size of the posts into the holes to manufacture the resin guide bridges.

4. In dental clinics, using single resin guide bridge and multiple guides to complete surgery is convenient.

5. Owing to the opening device of the guide, the external irrigation can be done during drilling. Thus preventing bone necrosis from over heating.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A positioning device for dental implant comprising
   a post being cylindrical and comprising a diameter adapted to correspond to a diameter of a hole in a dental model; and
   multiple guides being semi-tubular tabs, detachably mounted on the post and each guide comprising
      an inner concave;
      an inner diameter; and
      an outer diameter; and
   wherein the guides concentrically abut with each other and the inner diameter of an innermost one of the guides corresponds to the diameter of the post and the outer diameter of an inner one of any adjacent two of the guides corresponds to the inner diameter of an outer one of the adjacent two of the guides.

2. The positioning device for dental implant as claimed in claim 1, wherein the post is made of magnetic material.

3. The positioning device for dental implant as claimed in claim 1, wherein the post is made of permeable material.

4. The positioning device for dental implant as claimed in claim 1, wherein the guides are made of magnetic material.

5. The positioning device for dental implant as claimed in claim 1, wherein the outermost one of the guides further has at least one mounting hole defined transversely through the outermost one of the guides.

6. The positioning device for dental implant as claimed in claim 4, wherein the outermost one of the guides further has at least one mounting hole defined transversely through the outermost one of the guides.

* * * * *